US012060610B2

(12) United States Patent
Han

(10) Patent No.: US 12,060,610 B2
(45) Date of Patent: Aug. 13, 2024

(54) METHOD FOR EVALUATING AND COMPARING IMMUNOREPERTOIRES

(71) Applicant: iRepertoire, Inc., Huntsville, AL (US)

(72) Inventor: Jian Han, Huntsville, AL (US)

(73) Assignee: iRepertoire, Inc., Huntsville, AL (US)

( * ) Notice: Subject to any disclaimer, the term of this patent is extended or adjusted under 35 U.S.C. 154(b) by 0 days.

(21) Appl. No.: 14/089,517

(22) Filed: Nov. 25, 2013

(65) Prior Publication Data

US 2014/0127699 A1 May 8, 2014

Related U.S. Application Data

(63) Continuation of application No. 12/425,310, filed on Apr. 16, 2009, now Pat. No. 9,012,148.

(60) Provisional application No. 61/045,586, filed on Apr. 16, 2008.

(51) Int. Cl.
*C12Q 1/6883* (2018.01)
*C12Q 1/686* (2018.01)
*C12Q 1/6869* (2018.01)
*C12Q 1/6881* (2018.01)

(52) U.S. Cl.
CPC ........... *C12Q 1/6883* (2013.01); *C12Q 1/686* (2013.01); *C12Q 1/6869* (2013.01); *C12Q 1/6881* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,296,351 A | 3/1994 | Morley et al. | |
| 6,143,496 A | 11/2000 | Brown et al. | |
| 6,287,764 B1 * | 9/2001 | Hildebrand | C12Q 1/6881 |
| | | | 435/6.11 |
| 6,440,706 B1 | 8/2002 | Vogelstein et al. | |
| 7,741,463 B2 | 6/2010 | Gormley et al. | |
| 2002/0110807 A1 | 8/2002 | Pilarski et al. | |
| 2003/0120061 A1 | 6/2003 | Zhang | |
| 2006/0228350 A1 | 10/2006 | Wu et al. | |
| 2006/0234234 A1 * | 10/2006 | Van Dongen et al. | |
| 2007/0117134 A1 | 5/2007 | Kou | |
| 2008/0069770 A1 | 3/2008 | Hercend et al. | |
| 2008/0166704 A1 | 7/2008 | Marche et al. | |
| 2010/0151471 A1 | 6/2010 | Faham et al. | |
| 2010/0159456 A1 | 6/2010 | Albitar | |
| 2010/0167353 A1 | 7/2010 | Walder et al. | |
| 2010/0330571 A1 | 12/2010 | Robins et al. | |
| 2011/0003291 A1 | 1/2011 | Pasqual et al. | |
| 2012/0058902 A1 | 3/2012 | Livingston et al. | |

FOREIGN PATENT DOCUMENTS

| | | |
|---|---|---|
| EP | 1544308 B1 | 1/2009 |
| EP | 2062982 A1 | 5/2009 |
| WO | WO 2006/110855 * | 10/2006 |
| WO | WO 2009/095567 A2 | 8/2009 |
| WO | WO 2010/151416 A1 | 12/2010 |

OTHER PUBLICATIONS

Arstila et al., Science 286:958-961, Oct. 1999.*
Miqueu et al. Molecular Immunology 2007, 44:1057-1064.*
Akatsuka, et al. Rapid screening of T-cell receptor (TCR) variable gene usage by multiplex PCR: application for assessment of clonal composition. Tissue Antigens. Feb. 1999;53(2):122-34.
Arstila, et al. A direct estimate of the human alphabeta T cell receptor diversity. Science. Oct. 29, 1999;286(5441):958-61.
Bernardin, et al. Estimate of the total number of CD8+ clonal expansions in healthy adults using a new DNA heteroduplex-tracking assay for CDR3 repertoire analysis. J Immunol Methods. Mar. 1, 2003;274(1-2):159-75.
Blow. PCR's next frontier. Nature Methods. 2007; 4(10):869-875. doi:10.1038/nmeth1007-869.
Brenan, et al. High throughput, nanoliter quantitative PCR. Drug Discovery Today: Technologies. 2005; 2(3):247-253.
Buck, et al. Design strategies and performance of custom DNA sequencing primers. Biotechniques. Sep. 1999;27(3):528-36.
Dobosy, et al. RNase H-dependent PCR (rhPCR): improved specificity and single nucleotide polymorphism detection using blocked cleavable primers. BMC Biotechnol. Aug. 10, 2011;11:80. doi: 10.1186/1472-6750-11-80.
*Homo sapiens* germline beta T-cell receptor locus. NCBI Accession No. L36092. Jun. 26, 2009.
International Search Report and Written Opinion dated Mar. 22, 2013 for PCT/US2012/068617.
International Search Report and Written Opinion dated Mar. 28, 2013 for PCT/US2012/061193.
International Search Report and Written Opinion dated Apr. 10, 2012 for PCT/US2011/049012.
International Search Report and Written Opinion dated Sep. 23, 2013 for PCT/US2013/040221.
International Search Report and Written Opinion dated Oct. 20, 2011 for PCT/US2011/026373.
International Search Report and Written Opinion dated Oct. 25, 2013 for PCT/US2013/045994.
International Search Report and Written Opinion dated Nov. 25, 2013 for PCT/US2013/062925.
Kalinina, et al. Nanoliter scale PCR with TaqMan detection. Nucleic Acids Res. May 15, 1997;25(10): 1999-2004.
Lowe, et al. A computer program for selection of oligonucleotide primers for polymerase chain reactions. Nucleic Acids Res. Apr. 11, 1990;18(7):1757-61.
Maryanski, et al. A quantitative, single-cell PCR analysis of an antigen-specific TCR repertoire selected during an in vivo CD8 response: direct evidence for a wide range of clone sizes with uniform tissue distribution. Mol Immunol. Aug. 1999;36(11-12):745-53.

(Continued)

*Primary Examiner* — Samuel C Woolwine
(74) *Attorney, Agent, or Firm* — Butler Snow LLP

(57) ABSTRACT

Disclosed is a method for amplifying RNA and/or DNA from immune cell populations and using the amplified products to produce an immune response profile and evaluate the possible correlation between a normal or abnormal immune response and the development of a disease such as an autoimmune disease, cancer, diabetes, or heart disease.

6 Claims, 2 Drawing Sheets

Specification includes a Sequence Listing.

(56) References Cited

OTHER PUBLICATIONS

Nolan, et al. Quantification of mRNA using real-time RT-PCR. Nat Protoc. 2006;1(3):1559-82.
Office action dated Jan. 16, 2014 for U.S. Appl. No. 13/656,265.
Office action dated Apr. 4, 2014 for U.S. Appl. No. 12/794,507.
Office Action for Chinese Patent Application No. 201080028875.2, Mailed Feb. 13, 2014, 5 pages (With English Summary).
Puisieux, et al. Oligoclonality of tumor-infiltrating lymphocytes from human melanomas. J Immunol. Sep. 15, 1994;153(6):2807-18.
Robins, et al. Comprehensive assessment of T-cell receptor beta-chain diversity in alphabeta T cells. Blood. Nov. 5, 2009;114(19):4099-107. doi: 10.1182/blood-2009-04-217604. Epub Aug. 25, 2009.
Robins, et al. Overlap and effective size of the human CD8+ T cell receptor repertoire. Sci Transl Med. Sep. 1, 2010;2(47):47ra64. doi: 10.1126/scitranslmed.3001442.
Rozen, et al. Primer3 on the WWW for general users and for biologist programmers. Methods Mol Biol. 2000;132:365-86.
Van Der Velden, et al. Detection of minimal residual disease in hematologic malignancies by real-time quantitative PCR: principles, approaches, and laboratory aspects. Leukemia. Jun. 2003;17(6):1013-34.
Van Der Velden, et al. Real-time quantitative PCR for detection of minimal residual disease before allogeneic stem cell transplantation predicts outcome in children with acute lymphoblastic leukemia. Leukemia. Sep. 2001;15(9):1485-7.
Verhagen, et al. Application of germline IGH probes in real-time quantitative PCR for the detection of minimal residual disease in acute lymphoblastic leukemia. Leukemia. Aug. 2000;14(8):1426-35.
Lin, et al., "Multiplex genotype determination at a large number of gene loci," Proc. Natl. Acad. Sci. USA vol. 93, pp. 2582-2587, Mar. 1996.
Robins, et al., "Final Rejection issued Sep. 8, 2015," U.S. Appl. No. 14/242,299, filed Apr. 1, 2014.
Alexandre, D., et al. "*H. sapiens* rearranged T-cell receptor gamma chain gene, V3RS-J1 (hybrid joint)," GenBank accession No. X57740, NCBI, Feb. 11, 1997, 8 pages [online] [retrieved on Jun. 26, 2013] Retrieved from the internet <URL:http://www.ncbi.nlm.nih.gov/nuccore/x57740>.
Alexandre, D., et al. "*H. sapiens* rearranged T-cell receptor gamma chain gene, V2-JP1," GenBank accession No. X57737, NCBI, Nov. 14, 2006, 8 pages [online] [retrieved on Jun. 26, 2013] Retrieved from the internet <URL:http://www.ncbi.nlm.nih.gov/nuccore/x57737>.
Assaf, et al. High detection rate of T-cell receptor beta chain rearrangements in T-cell lymphoproliferations by family specific polymerase chain reaction in combination with the GeneScan technique and DNA sequencing. Blood. Jul. 15, 2000;96(2):640-6.
Bonarius, et al. Monitoring the T-cell receptor repertoire at single-clone resolution. PLoS One. Dec. 20, 2006;1:e55.
Duby, et al. Human T-cell receptor aberrantly rearranged beta-chain J1.5-Dx-J2.1 gene. Database NCBI [Online], GenBank Nucleotide, GenBank Accession No. M13574.1. May 15, 2008.

Freeman et al. Profiling the T-cell receptor beta-chain repertoire by massively parallel sequencing. Res. Oct. 2009;19(10):1817-24. doi: 10.1101/gr.092924.109. Epub Jun. 18, 20098.
Hwang, et al. Identification of a commonly used CDR3 region of infiltrating T cells expressing Vbeta13 and Vbeta15 derived from psoriasis patients. J Invest Dermatol. Mar. 2003;120(3):359-64.
Kiianitsa, et al. Development of Tools for T-Cell Repertoire Analysis (TCRB Spectratyping) for the Canine Model of Hematopoietic Cell Transplantation. Blood, ASH—Annual Meeting Abstracts, Nov. 2007, 110(11), Abstract 4873.
Kneba, et al. Analysis of rearranged T-cell receptor beta-chain genes by polymerase chain reaction (PCR) DNA sequencing and automated high resolution PCR fragment analysis. Blood. Nov. 15, 1995;86(10):3930-7.
Kneba, et al. Characterization of clone-specific rearrangement T-cell receptor gamma-chain genes in lymphomas and leukemias by the polymerase chain reaction and DNA sequencing. Blood. Jul. 15, 1994;84(2):574-81.
Lessin, et al. Molecular diagnosis of cutaneous T-cell lymphoma: polymerase chain reaction amplification of T-cell antigen receptor beta-chain gene rearrangements. J Invest Dermatol. Mar. 1991;96(3):299-302.
Mariani, et al. Comprehensive assessment of the TCRBV repertoire in small T-cell samples by means of an improved and convenient multiplex PCR method. Exp Hematol. Jun. 2009;37(6):728-38. doi: 10.1016/j.exphem.2009.03.003.
Maslanka, et al. Molecular Analysis of T-Cell Repertoires: Spectratypes Generated by Multiplex Polymerase Chain Reaction and Evaluated by Radioactivity or Fluorescence. Human Technology. Apr. 1995; 44(1):28-34.
Notice of allowance dated Oct. 10, 2013 for U.S. Appl. No. 12/794,507.
Office action dated Apr. 26, 2013 for U.S. Appl. No. 12/794,507.
Office action dated Nov. 7, 2012 for U.S. Appl. No. 12/794,507.
Office Action for European Patent Application No. EP 10722512.0, Dec. 17, 2012, 5 Pages.
Office Action for Israel Patent Application No. IL 217200, Jan. 21, 2013, 4 Pages.
PCT International Search Report and Written Opinion, PCT/US2010/037477, Sep. 24, 2010, 10 pages.
Santamaria, et al. Beta-cell-cytotoxic CD8+ T cells from nonobese diabetic mice use highly homologous T cell receptor alpha-chain CDR3 sequences. J Immunol. Mar. 1, 1995;154(5):2494-503.
Steenbergen, et al. Frequent ongoing T-cell receptor rearrangements in childhood B-precursor acute lymphoblastic leukemia: implications for monitoring minimal residual disease. Blood. Jul. 15, 1995;86(2):692-702.
Van Dongen, et al. Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia. Dec. 2003;17(12):2257-317.
Wang, et al. Quantitative measurement of pathogen-specific human memory T cell repertoire diversity using a CDR3 beta-specific microarray. BMC Genomics. Sep. 19, 2007;8:329.

* cited by examiner

Fig. 1
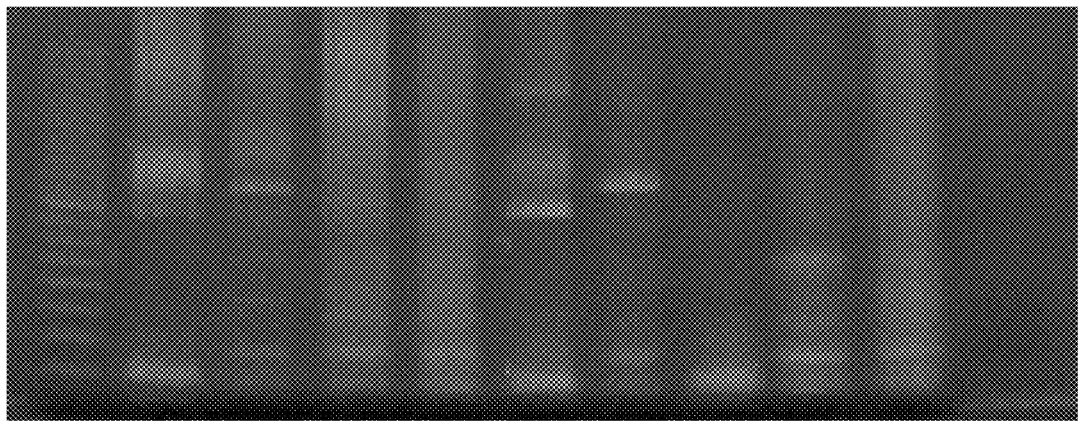
Fig. 1a
Fig. 1b
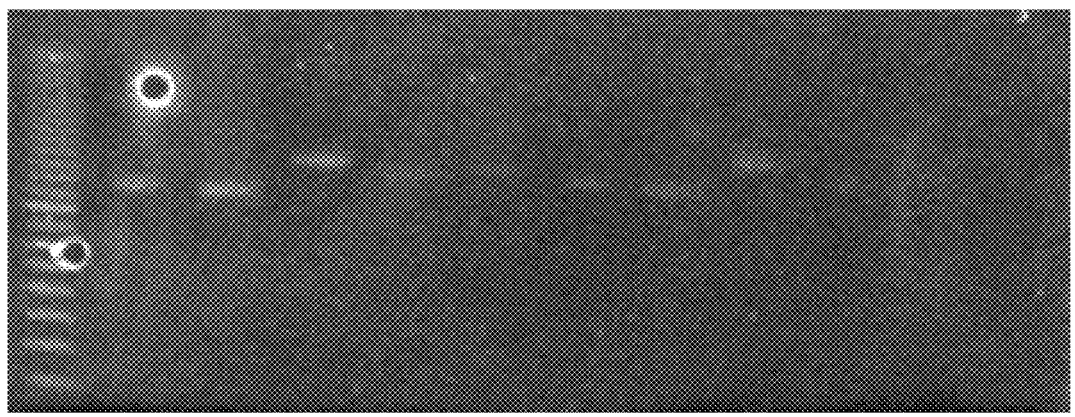

METHOD FOR EVALUATING AND COMPARING IMMUNOREPERTOIRES

CROSS-REFERENCE TO RELATED APPLICATIONS

This application is a continuation application of U.S. patent application Ser. No. 12/425,310, filed Apr. 16, 2009, which claims the benefit of priority of U.S. provisional patent application No. 61/045,586, filed Apr. 16, 2008.

FIELD OF THE INVENTION

The invention relates to methods for identifying biomarkers and to methods for identifying T-cell receptor, antibody, and MHC rearrangements in a population of cells.

BACKGROUND OF THE INVENTION

Scientists have known for a number of years that certain diseases are associated with particular genes or genetic mutations. Genetic causation, however, accounts for only a portion of the diseases diagnosed in humans. Many diseases appear to be linked in some way to the immune system's response to infectious and environmental agents, but how the immune system plays a role in diseases such as cancer, Alzheimer's, costochondritis, fibromyalgia, lupus, and other diseases is still being determined.

The human genome comprises a total number of 567-588 Ig (immunoglobulin) and TR (T cell receptor) genes (339-354 Ig and 228-234 TR) per haploid genome, localized in the 7 major loci. They comprise 405-418 V, 32 D, 105-109 J and 25-29 C genes. The number of functional Ig and TR genes is 321-353 per haploid genome. They comprise 187-216 V, 28 D, 86-88 J and 20-21 C genes (http://imgt.cines.fr). Through rearrangement of these genes, it has been estimated that approximately $2.5 \times 10^7$ possible antibodies or T cell receptors can be generated.

Although, at the germline level, human beings are capable of generating large numbers of diverse Igs and TRs, the number of available Igs and TRs for a particular individual is actually much smaller due to negative selection during B and T cell development. In some individuals, this process may not remove some of the cells that would cross-react with the body's own tissues, and this may be the cause of some types of autoimmune diseases.

A few diseases to date have been associated with the body's reaction to a common antigen (Prinz, J. et al., *Eur. J. Immunol.* (1999) 29(10): 3360-3368, "Selection of Conserved TCR VDJ Rearrangements in Chronic Psoriatic Plaques Indicates a Common Antigen in Psoriasis Vulgaris") and/or to specific VDJ rearrangements (Tamaru, J. et al., *Blood* (1994) 84(3): 708-715, "Hodgkin's Disease with a B-cell Phenotype Often Shows a VDJ Rearrangement and Somatic Mutations in the $V_H$ Genes"). What is needed is a better method for evaluating changes in human immune response cells and associating those changes with specific diseases.

SUMMARY OF THE INVENTION

The invention relates to a method for producing an immune status profile (ISP) for a human and/or animal. In one aspect of the invention, the method comprises the steps of amplifying, in a first amplification reaction using target-specific primers, at least one RNA and/or DNA from a sample of white blood cells from at least one human or animal subject to produce at least one amplicon, at least a portion of the target-specific primers comprising additional nucleotides to incorporate into a resulting amplicon a binding site for a common primer; rescuing the at least one amplicon from the first amplification reaction; amplifying, by the addition of common primers in a second amplification reaction, the amplicons of the first amplification reaction having at least one binding site for a common primer; and sequencing the amplicons of the second amplification reaction to identify and quantify DNA sequences representing antibody and/or receptor rearrangements to create an immune status profile.

In another aspect of the invention, the step of rescuing the at least one amplicon from the first amplification reaction may be omitted, and the first and second amplification reactions may occur without separation of the amplicons from the target-specific primers. Genomic DNA may also be amplified, and the step of amplifying DNA may be substituted for the step of amplifying RNA, especially in cases where analysis of an immune system component such as the major histocompatibility complex (MHC) is desired.

In aspects of the invention, subpopulations of white blood cells may be isolated by flow cytometry to separate naïve B cells, mature B cells, memory B cells, naïve T cells, mature T cells, and memory T cells. In various aspects of the method, recombinations in the subpopulation of cells are rearrangements of B-cell immunoglobulin heavy chain (IgH), kappa and/or lambda light chains (IgK, IgL), T-cell receptor Beta, Gamma, Delta, and/or Major Histocompatibility Complex (MHC) molecules I or II.

In another aspect of the invention, the method may also comprise compiling and comparing the immune cell profile for a population of normal individuals with the immune cell profile for a population of individuals who have been diagnosed with a disease to determine if there is a correlation between a specific rearrangement or set of rearrangements and the disease.

In another aspect of the invention, the method may comprise comparing the immune cell profile identified for a population of individuals to whom a vaccine has been administered with the immune cell profile for a population of individuals to whom the vaccine was not administered to evaluate the efficacy of the vaccine in producing an immune response.

BRIEF DESCRIPTION OF THE DRAWINGS

FIG. 1a and FIG. 1b are photographs of gels illustrating the presence of amplification products obtained by the method of the invention using primers disclosed herein.

DETAILED DESCRIPTION

Figure 2:
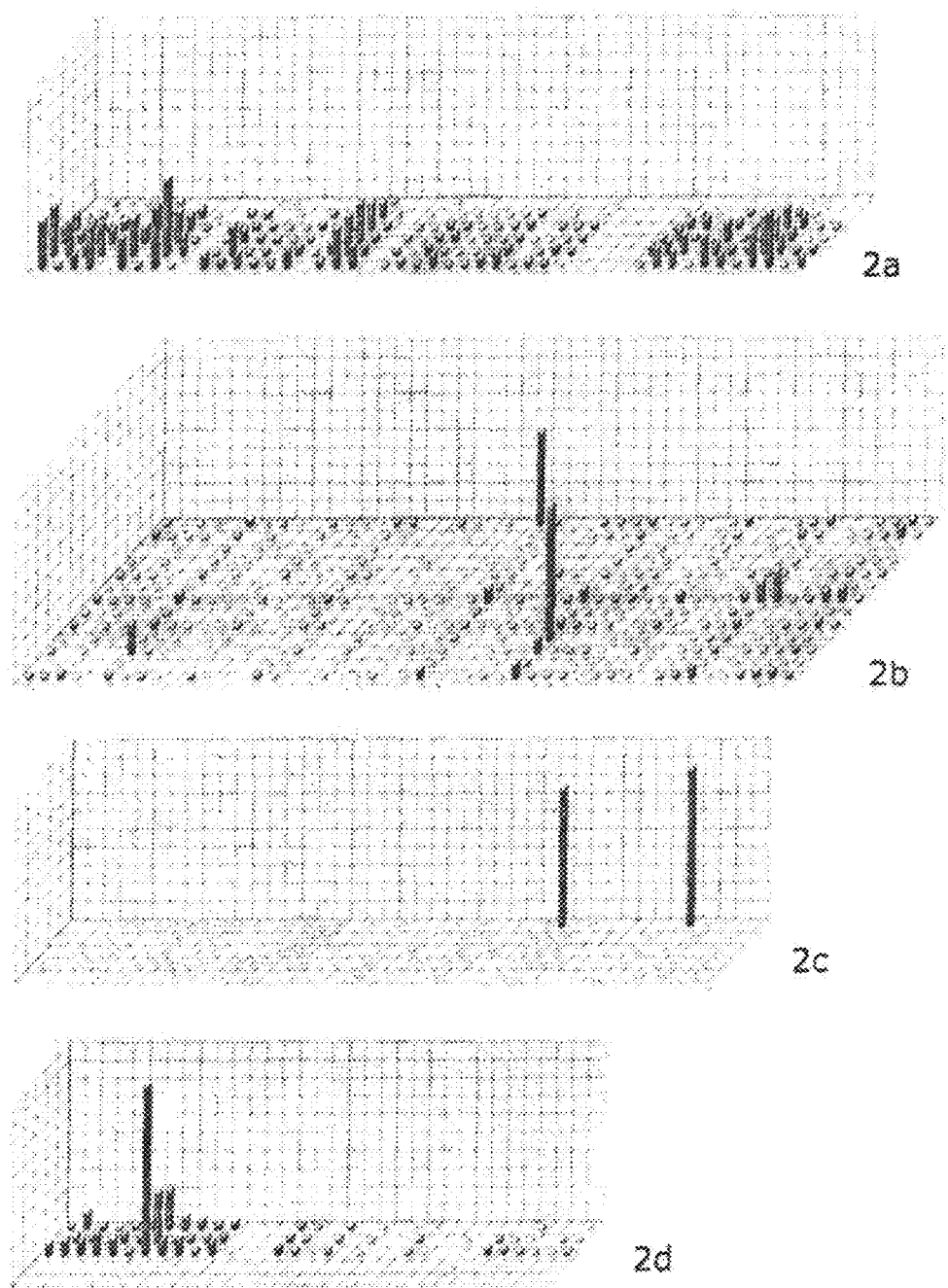
FIG. 2 illustrates distributions of domain usage for (a) Ig heavy chain in healthy control sample, (b) TCR beta chain in a blood sample from a patient with colon cancer, (c) Ig kappa chain in a blood sample from a patient with Chronic Lymphocytic Leukemia (CLL), and (d) Ig lambda chain in a blood sample from a patient with Systemic lupus erythematosus (SLE). Empty spots indicate missing sequences associated with corresponding V-J combinations and the height of the column indicates the frequency of occurrence of a particular sequence.

The inventor has developed a method for evaluating antibody and receptor rearrangements from a large number of cells, the method being useful for comparing rearrangements identified in populations of individuals to determine whether there is a correlation between a specific rearrangement or set of rearrangements and a disease, or certain symptoms of a disease. The method is also useful for establishing a history of the immune response of an individual or individuals in response to infectious and/or environmental agents, as well as for evaluating the efficacy of vaccines.

The invention relates to a method for producing an immune status profile (ISP) for a human and/or animal. In one aspect of the invention, the method comprises the steps of amplifying, in a first amplification reaction using target-specific primers, at least one RNA from a sample of white blood cells from at least one human or animal subject to produce at least one amplicon, at least a portion of the target-specific primers comprising additional nucleotides to incorporate into a resulting amplicon a binding site for a common primer; rescuing the at least one amplicon from the first amplification reaction; amplifying, by the addition of common primers in a second amplification reaction, the amplicons of the first amplification reaction having at least one binding site for a common primer; and sequencing the amplicons of the second amplification reaction to identify and quantify DNA sequences representing antibody and/or receptor rearrangements to create an immune status profile.

Where the term "comprising" is used herein, "consisting essentially of" and "consisting of" may also be used. The term "immune status profile" is intended to mean a profile for an individual or population of individuals indicating the presence and/or absence of sequences representing specific rearrangements representing the diversity of B cells, T cells, and/or other cells of the human and/or animal immune system, as well as the frequency of their occurrence. Where amplicons are referred to as "rescued" herein, it is to be understood that amplicon rescue may occur by the separation of amplicons from the primers which are used to create them, or may occur by dilution of the amplicon/primer mix so that, by virtue of the fact that there are significantly more amplicons than primers from a first amplification reaction, the effect of those primers is minimized in a second amplification reaction using different primers. "Common primers" are those primers that may be used to amplify polynucleotides (e.g., amplicons from a first amplification produced by target-specific primers) having non-identical sequences in general, but sharing sequence similarities in that they contain binding sites for the same primers. Common primers are generally chosen for their efficiency at priming successful amplifications, so their use is effective for achieving higher levels of amplification in a non-target-specific manner in the method of the present invention. Common primer binding sites may be incorporated into amplicons resulting from a first amplification by attaching their sequences or their complementary sequences to the sequence of a target-specific primer. Common primers may be chosen by one of skill in the art by a variety of primer-design methods.

Subpopulations of white blood cells may be isolated by flow cytometry to separate naïve B cells, mature B cells, memory B cells, naïve T cells, mature T cells, and memory T cells. Recombinations in these subpopulations of cells are generally rearrangements of B-cell immunoglobulin heavy chain (IgH), kappa and/or lambda light chains (IgK, IgL), T-cell receptor Beta, Gamma, Delta, and/or Major Histocompatibility Complex (MHC) molecules I or II.

By performing an additional step, namely that of compiling and comparing the average immune status profile for a population of normal individuals with an average immune status profile for a population of individuals who have been diagnosed with a disease, it is possible to use the immune cell profile to determine if there is a correlation between a specific rearrangement or set of rearrangements and the disease.

The invention also provides a method for evaluating vaccine efficacy, in terms of creating a change in the immune cell profile, by performing the steps of the method and comparing the immune cell profile identified for a population of individuals to whom a vaccine has been administered with the immune cell profile for a population of individuals to whom the vaccine was not administered to evaluate the efficacy of the vaccine in producing an immune response.

In one embodiment of the invention, a peripheral blood sample is taken from a patient and isolation of a subpopulation of white blood cells may be performed by flow cytometry to separate naïve B cells, mature B cells, memory B cells, naïve T cells, mature T cells, and memory T cells. In various embodiments of the method, recombinations in the subpopulation of cells may comprise rearrangements of B-cell immunoglobulin heavy chain (IgH), kappa and/or lambda light chains (IgK, IgL), T-cell receptor Beta, Gamma, Delta, or Major Histocompatibility Complex (MHC) molecules I or II.

In some aspects, the step of rescuing the amplicons from the first amplification reaction may be omitted and the two amplification reactions may be performed in the same reaction tube without amplicon rescue or dilution of the primers remaining from the first amplification reaction.

The inventor previously developed a PCR method known as tem-PCR, which has been described in publication number WO2005/038039. More recently, the inventor has developed a method called amplicon rescue multiplex polymerase chain reaction (arm-PCR), which is described in U.S. PCT/US09/39552 and herein. Both the tem-PCR and arm-PCR methods provide semi-quantitative amplification of multiple polynucleotides in one reaction. Additionally, arm-PCR provides added sensitivity. Both provide the ability to amplify multiple polynucleotides in one reaction, which is beneficial in the present method because the repertoire of various T and B cells, for example, is so large. The addition of a common primer binding site in the amplification reaction, and the subsequent amplification of target molecules using common primers, gives a quantitative, or semi-quantitative result— making it possible to determine the relative amounts of the cells comprising various rearrangements within a patient blood sample. Clonal expansion due to recognition of antigen results in a larger population of cells which recognize that antigen, and evaluating cells by their relative numbers provides a method for determining whether an antigen exposure has influenced expansion of antibody-producing B cells or receptor-bearing T cells. This is helpful for evaluating whether there may be a particular population of cells that is prevalent in individuals who have been diagnosed with a particular disease, for example, and may be especially helpful in evaluating whether or not a vaccine has achieved the desired immune response in individuals to whom the vaccine has been given.

There are several commercially available high throughput sequencing technologies, such as Roche Life Sciences 454 Sequencing®. In this sequencing method, 454A and 454B primers are either linked onto PCR products during PCR or ligated on after the PCR reaction. When done in conjunction with tem-PCR or arm-PCR, 454A and 454B primers may be used as common primers in the amplification reactions. PCR products, usually a mixture of different sequences, are diluted to about 200 copies per µl. In an "emulsion PCR" reaction, (a semisolid gel like environment) the diluted PCR products are amplified by primers (454A or 454B) on the surface of the microbeads. Because the PCR templates are so dilute, usually only one bead is adjacent to one template, and confined in the semisolid environment, amplification only occurs on and around the beads. The beads are then eluted and put onto a plate with specially designed wells. Each well can only hold one bead. Reagents are then added into the wells to carry out pyrosequencing. A fiber-optic detector may be used to read the sequencing reaction from each well and the data is collected in parallel by a computer. One such high throughput reaction could generate up to 60 million reads (60 million beads) and each read can generate about 300 bp sequences.

One aspect of the invention involves the development of a database of immune status profiles, or "personal immunorepertoires" (PIRs), so that each individual may establish a baseline and follow the development of immune responses to antigens, both known and unknown, over a period of years. This information may, if information is gathered from a large number of individuals, provide an epidemiological database that will produce valuable information, particularly in regard to the development of those diseases such as cancer and heart disease which are thought to often arise from exposure to viral or other infectious agents, many of which have as yet been unidentified. One particularly important use for the method of the invention enables studies of children to determine whether infectious disease, environmental agents, or vaccines may be the cause of autism. For example, many have postulated that vaccine administration may trigger the development of autism. However, many also attribute that potential correlation to the use of agents such as thimerosol in the vaccine, and studies have demonstrated that thimerosol does not appear to be a causative agent of the disease. There is still speculation that the development of cocktail vaccines has correlated with the rise in the number of cases of autism, however, but gathering data to evaluate a potential causal connection for multiple antigens is extremely difficult. The method of the present invention simplifies that process and may provide key information for a better understanding of autism and other diseases in which the immune response of different individuals may provide an explanation for the differential development of disease in some individuals exposed to an agent or a group of agents, while others similarly exposed do not develop the disease.

Imbalances of the PIR, triggered by infection, may lead to many diseases, including cancers, leukemia, neuronal diseases (Alzheimer's, Multiple Sclerosis, Parkinson's, autism etc), autoimmune diseases, and metabolic diseases. These diseases may be called PIR diseases. There may be two PIR disease forms. (1) a "loss of function" form, and (2) a "gain of function" form. In the "loss of function" form, a person is susceptible to a disease because his/her restricted and/or limited PIR lacks the cells that produce the most efficient and necessary Igs and TRs. In the "gain of function" form, a person is susceptible to a disease because his/her PIR gained cells that produce Igs and TRs that normally should not be there. In the "loss of function" (LOF) PIR diseases, an individual does not have the appropriate functional B or T cells to fight a disease. His/her HLA typing determines that those cells are eliminated during the early stages of the immune cell maturation process, the cells generally being eliminated because they react to strongly to his/her own proteins.

One aspect of the invention also comprises entering a patient immune cell profile into a database in combination with identifying information such as, for example, a patient identification number, a code comprising the patient's HLA type, a disease code comprising one or more clinical diagnoses that may have been made, a "staging code" comprising the date of the sample, a cell type code comprising the type of cell subpopulation from which the RNA was amplified and sequenced, and one or more sequence codes comprising the sequences identified for the sample.

The described method includes a novel primer set that not only allows amplification of the entire immunorepertoire, but also allows multiplex amplification that is semi-quantitative. Multiplex amplification requires that only a few PCR or RT-PCR reactions are needed. For example, all immunoglobulin (Ig) sequences present may be amplified in one reaction, or two or three reactions may be performed separately, using primers specific for IgH, IgL or IgK. Similarly, the T-cell receptors (TRs) may be amplified in just one reaction, or may be amplified in a few reactions including the T-cell receptors designated TRA, TRB, TRD, and TRG. MHC genes may be amplified in just one PCR reaction. Semi-quantitative amplification allows all the targets in the multiplex reaction to be amplified independently, so that the end point analysis of the amplified products will reflect the original internal ratio among the targets. Because this ratio is maintained, it is possible to produce an immune cell profile that indicates the presence or absence, as well as relative numbers, of various immune system cells. Amplification of RNA according to the method of the invention may be performed using any or all of the primers listed in Tables 1, 2, and/or 3. The invention therefore provides a method for using at least one (which may, of course, more preferably include a least 2, at least 3, at least 4, etc.) primers chosen from among the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO:138, SEQ ID NO: 139, SEQ ID NO: 140, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, and combinations thereof, to perform a first amplification producing at least one first amplicon, at least one of the target-specific primers containing additional base pairs so that the amplification results in the addition of a binding sequence for at least one common primer into the at least one first amplicon; amplifying the at least one first amplicon in a second amplification using at least one common primer to produce at least one second amplicon; and sequencing the at least one second amplicon to identify and quantify the sequences produced by the first and second amplifications. The listed primers were designed by the inventor to provide efficient amplification of their respective RNA and/or DNA targets. Use of the entire group of primers is effective to produce a detailed immune status profile for an individual. Use of a subset may, however, be desired when specific populations of T or B cells, for example, are the subject of particular interest.

By way of further explanation, the following example may be illustrative of the methods of the invention. Blood samples may be taken from children prior to administration of any vaccines, those blood samples for each child being used in the method of the invention to create a "baseline" immune status profile or personal immunorepertoire (PIR) from which future immune cell profiles, created from blood samples taken during later years and analyzed by the method of the invention, may be compared. For each child, the future samples may be utilized to determine whether there has been an exposure to an agent which has expanded a population of cells known to be correlated with a disease, and this may serve as a "marker" for the risk of development of the disease in the future. Individuals so identified may then be more closely monitored so that early detection is possible, and any available treatment options may be provided at an earlier stage in the disease process.

The method of the invention may be especially useful for identifying commonalities between individuals with autoimmune diseases, for example, and may provide epidemiological data that will better describe the correlation between infectious and environmental factors and diseases such as heart disease, atherosclerosis, diabetes, and cancer—providing biomarkers that signal either the presence of a disease, or the tendency to develop disease.

The method may also be useful for development of passive immunity therapies. For example, following exposure to an infectious agent, certain antibody-producing B cells and/or T cells are expanded. The method of the invention enables the identification of protective antibodies, for example, and those antibodies may be utilized to provide passive immunity therapies in situations where such therapy is needed.

The method of the invention may also provide the ability to accomplish targeted removal of cells with undesirable rearrangements, the method providing a means by which such cells rearrangements may be identified.

The inventor has identified and developed target-specific primers for use in the method of the invention. T-cell-specific primers are shown in Table 1, antibody-specific primers are shown in Table 2, and HLA-specific primers are shown in Table 3. Therefore, the method may comprise using any combination of primers of Table 1, Table 2, and/or Table 3 to amplify RNA and/or DNA from a blood sample, and more particularly to identify antibodies, T-cell receptors, and HLA molecules within a population of cells. For example, an analysis of T-cell distribution might utilize all or a portion of the primers listed in Table 1 (SEQ ID NO: 1 through SEQ ID NO: 157). An analysis of Ig might utilize all or a portion of the primers listed in Table 2 (SEQ ID NO: 158 through SEQ ID NO: 225), and an analysis of HLA distribution might utilize all or a portion of the primers listed in Table 3 (SEQ ID NO: 159 through SEQ ID NO: 312).

In a tem-PCR reaction, nested gene-specific primers are designed to enrich the targets during initial PCR cycling. Later, universal "Super" primers are used to amplify all targets. Primers are designated as $F_o$ (forward out), $F_i$ (forward in), $R_i$ (reverse in), $R_o$ (reverse out), FS (forward super primer) and RS, (reverse super primer), with super primers being common to a variety of the molecules due to the addition of a binding site for those primers at the end of a target-specific primer. The gene-specific primers ($F_i$, $F_i$, $R_i$, and $R_o$) are used at extremely low concentrations. Different primers are involved in the tem-PCR process at each of the three major stages. First, at the "enrichment" stage, low-concentration gene-specific primers are given enough time to find the templates. For each intended target, depending on which primers are used, four possible products may be generated: $F_o/R_o$, $F_i/R_i$, $F_i/R_i$, and $F_o/R_i$. The enrichment stage is typically carried out for 10 cycles. In the second, or "tagging" stage, the annealing temperature is raised to 72° C., and only the long 40-nucleotide inside primers (Fi and Ri) will work. After 10 cycles of this tagging stage, all PCR products are "tagged" with the universal super primer sequences. Then, at the third "amplification" stage, high-concentration super primers work efficiently to amplify all targets and label the pCR products with biotin during the process. Specific probes may be covalently linked with Luminex® color-coated beads.

To amplify the genes coding for immunoglobulin super-family molecules, the inventor designed nested primers based on sequence information available in the public domain. For studying B and T cell VDJ rearrangement, the inventor designed primers to amplify rearranged and expressed RNAs. Generally, a pair of nested forward primers is designed from the V genes and a set of reverse nested primers are designed from the J or C genes. The average amplicon size is 250-350 bp. For the IgHV genes, for example, there are 123 genes that can be classified into 7 different families, and the present primers are designed to be family-specific. However, if sequencing the amplified cDNA sequences, there are enough sequence diversities to allow further differentiation among the genes within the same family. For the MHC gene locus, the intent is to amplify genomic DNA.

The invention may be further described by means of the following non-limiting examples.

EXAMPLES

Amplification of T or B Cell Rearrangement Sites

All oligos were resuspended using 1× TE. All oligos except 454A and 454B were resuspended to a concentration of 100 pmol/μL. 454A and 454B were resuspended to a concentration of1000 pmol/μL 454A and 454B are functionally the same as the common primers described previously, the different sequences were used for follow up high throughput sequencing procedures.

Three different primer mixes were made. An Alpha Delta primer mix included 82 primers (all of TRAV-C+TRDV-C), a Beta Gamma primer mix included 79 primers (all of TRBVC and TRGV-C) and a B cell primer mix that included a total of 70 primers. $F_o$, $F_i$, and $R_i$ primers were at a concentration of 1 pmol/μL. $R_o$ primers were at a concentration of 5 pmol/μL. 454A and 454B were at a concentration of 30 pmol/μL.

Three different RNA samples were ordered from ALL-CELLS (www.allcells.com). All samples were diluted down to a final concentration of 4 ng/μL. The samples used were: ALL-PB-MNC (from a patient with acute lymphoblastic leukemia), NPB-Pan T Cells (normal T cells) and NPB-B Cells (normal B cells).

RT-PCR was performed using a Qiagen® One-Step RT-PCR kit. Each sample contained the following:
 10 μL of Qiagen® Buffer
 2 μL of DNTP's
 2 μl of Enzyme
 23.5 μL of dH2O
 10 μL of the appropriate primer mix
 2.5 μL of the appropriate template (long of RNA total)
The samples were run using the following cycling conditions:
 50° C. for 30 minutes
 95° C. for 15 minutes
 94° C. for 30 seconds
 15 cycles of
  55° C. for 1 minute
  72° C. for 1 minute
  94° C. for 15 seconds
 6 cycles of
  70° C. for 1 minute 30 seconds
  94° C. for 15 seconds
 30 cycles of
  55° C. for 15 seconds
  72° C. for 15 seconds
  72° C. for 3 minutes
  4° C. Hold The order of samples placed in the gel shown in FIG. 1a was: (1) Ladder (500 bp being the largest working down in steps of 20 bp, the middle bright band in FIG. 1a is 200 bp); (2) α+δ primer mix with 10 ng Pan T Cells Template; (3) β+γ primer mix with 10 ng Pan T Cells Template; (4) B Cell primer mix with 10 ng B Cells Template; (5) B Cell primer mix with 10 ng ALL Cells Template; (6) α+δ primer mix with 10 ng ALL Cells Template; (7) β+γ primer mix with 10 ng ALL Cells Template; 8. α+δ primer mix blank; (9) β+γ primer mix blank; (10) B Cell primer mix blank; (11) Running buffer blank. These samples were run on a pre-cast ClearPAGE® SDS 10% gel using 1× ClearPAGE® DNA native running buffer.

The initial experiment showed that a smear is generated from PCR reactions where templates were included. The smears indicate different sizes of PCR products were generated that represented a mixture of different VDJ rearrangements. There was some background amplification from the B cell reaction. Further improvement on that primer mix cleaned up the reaction.

To determine whether the PCR products indeed include different VDJ rearrangements, it was necessary to isolate and sequence the single clones. Instead of using the routine cloning procedures, the inventor used a different strategy. PCR products generated from the Alpha Delta mix and the Beta Gamma mix (lanes 2 and 3 in FIG. 1a) were diluted 1:1000 and a 2 μl aliquot used as PCR template in the following reaction. Then, instead of using a mixture of primers that targeting the entire repertoire, one pair of specific $F_i$ and $R_i$ primers were used (5 pmol each) to amplify only one specific PCR product. The following cycling conditions were used to amplify the samples:
 95° C. for 5 minutes
 30 cycles of
  94° C. for 30 seconds
  72° C. for 1 minute
  72° C. for 3 minutes
  4° C. hold A Qiagen PCR kit was used to amplify the products. The Master Mix used for the PCR contained the following: 5 μL 10× PCR Buffer, 1 μL dNTP, 0.25 μL HotStartTaq Plus, and 39.75 μL H$_2$O. (For a mix for 12 reactions: 60 μL 10× PCR Buffer, 12 μL dNTP, 3 μL HotStartTaq Plus, and 477 μL H$_2$O.)

The photograph of the gel in FIG. 1b shows the PCR products of the following reactions: (1) Ladder; (2) TRAV1F$_i$+TRACR$_i$ with alpha delta Pan T PCR product; (3) TRAV2F$_i$+TRACR$_i$ with alpha delta Pan T PCR product; (4) TRAV3F$_i$+TRACR$_i$ with alpha delta Pan T PCR product; (5) TRAV4F$_i$+TRACR$_i$ with alpha delta Pan T PCR product; (6) TRAV5F$_i$+TRACR$_i$ with alpha delta Pan T PCR product; (7) TRAV1F$_i$+TRACR$_i$ with alpha delta Pan T PCR product; (8) TRAV2F$_i$+TRACR$_i$ with alpha delta Pan T PCR product; (9) TRAV3F$_i$+TRACR$_i$ with alpha delta Pan T PCR product; (10) TRAV4F$_i$+TRACR$_i$ with alpha delta Pan T PCR product; (11) TRAV5F$_i$+TRACR$_i$ with alpha delta Pan T PCR product; (12) PCR Blank. Primers listed as F$_1$ are "forward inner" primers and primers listed as $F_o$ are "forward outer" primers, with $R_i$ and $R_o$ indicating "reverse inner" and "reverse outer" primers, respectively.

As illustrated by FIG. 1b, a single PCR product was generated from each reaction. Different size bands were generated from different reactions. This PCR cloning approach is successful for two major reasons—(1) The PCR templates used in this reaction were diluted PCR products (1:1000) of previous reactions that used primer mixes to amplify all possible VDJ rearrangements (for example, a primer mix was used that included total of 82 primers to amplify T cell receptor Alpha and Delta genes) and (2) Only one pair of PCR primers, targeting a specific V gene, are used in each reaction during this "cloning" experiment. In every case, a single clone was obtained, and a specific T cell receptor V gene that matched the $F_i$ primer was identified.

Sequencing of Immune Cell RNA Using Primers of SEQ ID NO: 1-SEQ ID NO: 312

Pan-T, pan-B, and neutrophil isolation was performed using super-paramagnetic polystyrene beads coated with monoclonal antibody specific for certain cell types (Dynabeads®, Invitrogen Corp., Carlsbad, California) following manufacturer's instructions. Anti-CD3 beads were used to isolate pan-T cells, anti-CD19 beads for pan-B cells, and anti-CD15 beads for neutrophils. Isolated cells were resuspended in 300 µl RNAProtect® (Qiagen) reagent and counted using a hemacytometer.

T cell subpopulations were isolated from a normal patient 48-year-old Asian male. PMBCs were obtained from 40 ml of whole blood collected in sodium heparin by density centrifugation over Ficoll Prep Plus Reagent. Pan-T cells were isolated from the mononuclear layer using a magnetic bead isolation kit (Miltenyi Biotec, Auburn, California), following manufacturer's instructions. Anti-CD4 and anti-CD25 beads were used to isolate regulatory T cells, anti-CD56 for NKT cells, anti-CD8 for cytotoxic T cells, and anti-CD4 and anti-CD294 for Th2 cells. Th1 cells were isolated via negative selection. A separate 40 ml sample of whole blood collected in sodium heparin was used to obtain naive, activated, and memory T cell subpopulations. Anti-CD45RA beads were used to isolate naive T cells, anti-CD69 for activated T cells and anti-CD45R0 beads for memory T cells. Isolated cells were re-suspended in 300 µl of RNAProtect® reagent (Qiagen). Cells were counted using a hemacytometer.

DNA extraction from the isolated neutrophils was performed using a QIAmp® DNA mini kit (Qiagen) using the protocol provided by the manufacturer. RNA was extracted from T cell subsets using an RNeasy® kit (Qiagen) according to the protocol provided by the manufacturer. The concentrations of extracted DNA and RNA were measured using Nanodrop® technology (Nanodrop Technologies, Wilmington, Delaware). Samples were stored at −80° C.

RT-PCR was performed according to the method of the invention using nested PCR to amplify multiple targets and target-specific primers to incorporate a common primer binding sequence into the resulting amplicons in a first amplification reaction. Common primers were then used in a second amplification reaction to exponentially amplify the amplicons rescued from the first amplification reaction while preserving the relative ratios of each amplicon. PCR was performed using a One-Step RT-PCR kit (Qiagen). DNA amplification for HLA typing was similarly performed, but with a mulitplex PCR kit (Qiagen). Each amplicon mixture was subjected to high-throughput sequencing with the Roche 454 sequencing platform.

More than 1.6 million effective sequences were generated for one single individual (normal 48-year-old Asian male) by sampling different subpopulations of lymphocytes in peripheral blood at different time points. Additionally, 170,734 effective sequences were generated for the colon cancer, CLL, SLE, and a second healthy patient (a 32-year-old Caucasian male). The number of unique reads generated in this study was compared to the number of unique reads existing in public databases in Table 1. The public sequence data set was compiled by searching Genbank nucleotide database with terms of 'human[orgn] AND (immunoglobulin[titl] OR T-cell receptor[titl]) AND mRNA[titl]'. In addition, the annotated IMGT/LIGM-DB (Brezinschek et al, 1995) cDNA sequences were gathered with a Python script. The two data sets were merged, and one copy was kept for any redundant sequences.

Biased usage of V, and J gene segments in a healthy control, CLL, colon cancer, and SLE sample was analyzed. The bias of domain usage was particularly outstanding for TCR beta chain in the colon cancer sample and SLE sample, while in the healthy control sample the domain usage is quite normal without significant bias to any particular domain. It was evident that colon cancer and SLE profiles not only show clonal expansion, but demonstrate the loss of overall diversity, as well.

The distribution of functional germline V, J gene segments seen in the pan-T and pan-B populations from normal patient indicated that 87.2% of potential combinations have sequences observed. Only IGHV3-d was not observed in this investigation, while TRBV4-3, IGHV3-d, IGHV4-30-4 and IGHV4-31 and IGHL3-22 were observed in other samples with extremely low frequency. Previous research did not reveal any cDNA sequence data related to IGHV3-d, which suggests that IGHV3-d may be used infrequently. Some sequences were present in high (e.g. 1000) numbers, while others were present in significantly lower numbers. The inventor believes that higher numbers represent lymphocyte clonal expansions, reflecting the real immune responses in the subject. Studies of VH gene distribution in normal individuals have previously found the frequency of usage in general to be similar to the germline complexity, while many immune responses show some level of bias in the usage of V, D and J gene segments.

TABLE 1

| Primer | Sequence | Sequence ID Number |
|---|---|---|
| TRAV1Fo | 5'-TGCACGTACCAGACATCTGG-3' | SEQ ID NO: 1 |
| TRAV1Fi | AGGTCGTTTTTCTTCATTCC | SEQ ID NO: 2 |
| TRAV2Fo | TCTGTAATCACTCTGTGTCC | SEQ ID NO: 3 |
| TRAV2Fi | AGGGACGATACAACATGACC | SEQ ID NO: 4 |
| TRAV3Fo | CTATTCAGTCTCTGGAAACC | SEQ ID NO: 5 |
| TRAV3Fi | ATACATCACAGGGGATAACC | SEQ ID NO: 6 |
| TRAV4Fo | TGTAGCCACAACAACATTGC | SEQ ID NO: 7 |
| TRAV4Fi | AAAGTTACAAACGAAGTGGC | SEQ ID NO: 8 |
| TRAV5Fo | GCACTTACACAGACAGCTCC | SEQ ID NO: 9 |
| TRAV5Fi | TATGGACATGAAACAAGACC | SEQ ID NO: 10 |
| TRAV6Fo | GCAACTATACAAACTATTCC | SEQ ID NO: 11 |

TABLE 1-continued

| Primer | Sequence | Sequence ID Number |
|---|---|---|
| TRAV6Fi | GTTTTCTTGCTACTCATACG | SEQ ID NO: 12 |
| TRAV7Fo | TGCACGTACTCTGTCAGTCG | SEQ ID NO: 13 |
| TRAV7Fi | GGATATGAGAAGCAGAAAGG | SEQ ID NO: 14 |
| TRAV8Fo | AATCTCTTCTGGTATGTSCA | SEQ ID NO: 15 |
| TRAV8Fi | GGYTTTGAGGCTGAATTTA | SEQ ID NO: 16 |
| TRAV9Fo | GTCCAATATCCTGGAGAAGG | SEQ ID NO: 17 |
| TRAV9Fi | AACCACTTCTTTCCACTTGG | SEQ ID NO: 18 |
| TRAV10Fo | AATGCAATTATACAGTGAGC | SEQ ID NO: 19 |
| TRAV10Fi | TGAGAACACAAAGTCGAACG | SEQ ID NO: 20 |
| TRAV11Fo | TCTTAATTGTACTTATCAGG | SEQ ID NO: 21 |
| TRAV11Fi | TCAATCAAGCCAGAAGGAGC | SEQ ID NO: 22 |
| TRAV12Fo | TCAGTGTTCCAGAGGGAGCC | SEQ ID NO: 23 |
| TRAV12Fi | ATGGAAGGTTTACAGCACAG | SEQ ID NO: 24 |
| TRAV13Fo | ACCCTGAGTGTCCAGGAGGG | SEQ ID NO: 25 |
| TRAV13Fi | TTATAGACATTCGTTCAAAT | SEQ ID NO: 26 |
| TRAV14Fo | TGGACTGCACATATGACACC | SEQ ID NO: 27 |
| TRAV14Fi | CAGCAAAATGCAACAGAAGG | SEQ ID NO: 28 |
| TRAV16Fo | AGCTGAAGTGCAACTATTCC | SEQ ID NO: 29 |
| TRAV16Fi | TCTAGAGAGCATCAAAGG | SEQ ID NO: 30 |
| TRAV17Fo | AATGCCACCATGAACTGCAG | SEQ ID NO: 31 |
| TRAV17Fi | GAAAGAGAGAAACACAGTGG | SEQ ID NO: 32 |
| TRAV18Fo | GCTCTGACATTAAACTGCAC | SEQ ID NO: 33 |
| TRAV18Fi | CAGGAGACGGACAGCAGAGG | SEQ ID NO: 34 |
| TRAV19Fo | ATGTGACCTTGGACTGTGTG | SEQ ID NO: 35 |
| TRAV19Fi | GAGCAAAATGAAATAAGTGG | SEQ ID NO: 36 |
| TRAV20Fo | ACTGCAGTTACACAGTCAGC | SEQ ID NO: 37 |
| TRAV20Fi | AGAAAGAAAGGCTAAAAGCC | SEQ ID NO: 38 |
| TRAV21Fo | ACTGCAGTTTCACTGATAGC | SEQ ID NO: 39 |
| TRAV21Fi | CAAGTGGAAGACTTAATGCC | SEQ ID NO: 40 |
| TRAV22Fo | GGGAGCCAATTCCACGCTGC | SEQ ID NO: 41 |
| TRAV22Fi | ATGGAAGATTAAGCGCCACG | SEQ ID NO: 42 |
| TRAV23Fo | ATTTCAATTATAAACTGTGC | SEQ ID NO: 43 |
| TRAV23Fi | AAGGAAGATTCACAATCTCC | SEQ ID NO: 44 |
| TRAV24Fo | GCACCAATTTCACCTGCAGC | SEQ ID NO: 45 |
| TRAV24Fi | AGGACGAATAAGTGCCACTC | SEQ ID NO: 46 |
| TRAV25Fo | TCACCACGTACTGCAATTCC | SEQ ID NO: 47 |
| TRAV25Fi | AGACTGACATTTCAGTTTGG | SEQ ID NO: 48 |
| TRAV26Fo | TCGACAGATTCMCTCCCAGG | SEQ ID NO: 49 |

TABLE 1-continued

| Primer | Sequence | Sequence ID Number |
|---|---|---|
| TRAV26Fi | GTCCAGYACCTTGATCCTGC | SEQ ID NO: 50 |
| TRAV27Fo | CCTCAAGTGTTTTTCCAGC | SEQ ID NO: 51 |
| TRAV27Fi | GTGACAGTAGTTACGGGTGG | SEQ ID NO: 52 |
| TRAV29Fo | CAGCATGTTTGATTATTTCC | SEQ ID NO: 53 |
| TRAV29Fi | ATCTATAAGTTCCATTAAGG | SEQ ID NO: 54 |
| TRAV30Fo | CTCCAAGGCTTTATATTCTG | SEQ ID NO: 55 |
| TRAV30Fi | ATGATATTACTGAAGGGTGG | SEQ ID NO: 56 |
| TRAV34Fo | ACTGCACGTCATCAAAGACG | SEQ ID NO: 57 |
| TRAV34Fi | TTGATGATGCTACAGAAAGG | SEQ ID NO: 58 |
| TRAV35Fo | TGAACTGCACTTCTTCAAGC | SEQ ID NO: 59 |
| TRAV35Fi | CTTGATAGCCTTATATAAGG | SEQ ID NO: 60 |
| TRAV36Fo | TCAATTGCAGTTATGAAGTG | SEQ ID NO: 61 |
| TRAV36Fi | TTTATGCTAACTTCAAGTGG | SEQ ID NO: 62 |
| TRAV38Fo | GCACATATGACACCAGTGAG | SEQ ID NO: 63 |
| TRAV38Fi | TCGCCAAGAAGCTTATAAGC | SEQ ID NO: 64 |
| TRAV39Fo | TCTACTGCAATTATTCAACC | SEQ ID NO: 65 |
| TRAV39Fi | CAGGAGGGACGATTAATGGC | SEQ ID NO: 66 |
| TRAV40Fo | TGAACTGCACATACACATCC | SEQ ID NO: 67 |
| TRAV40Fi | ACAGCAAAAACTTCGGAGGC | SEQ ID NO: 68 |
| TRAV41Fo | AACTGCAGTTACTCGGTAGG | SEQ ID NO: 69 |
| TRAV41Fi | AAGCATGGAAGATTAATTGC | SEQ ID NO: 70 |
| TRACRo | GCAGACAGACTTGTCACTGG | SEQ ID NO: 71 |
| TRACRi | AGTCTCTCAGCTGGTACACG | SEQ ID NO: 72 |
| TRBV1Fo | AATGAAACGTGAGCATCTGG | SEQ ID NO: 73 |
| TRBV1Fi | CATTGAAAACAAGACTGTGC | SEQ ID NO: 74 |
| TRBV2Fo | GTGTCCCCATCTCTAATCAC | SEQ ID NO: 75 |
| TRBV2Fi | TGAAATCTCAGAGAAGTCTG | SEQ ID NO: 76 |
| TRBV3Fo | TATGTATTGGTATAAACAGG | SEQ ID NO: 77 |
| TRBV3Fi | CTCTAAGAAATTTCTGAAGA | SEQ ID NO: 78 |
| TRBV4Fo | GTCTTTGAAATGTGAACAAC | SEQ ID NO: 79 |
| TRBV4Fi | GGAGCTCATGTTTGTCTACA | SEQ ID NO: 80 |
| TRBV5Fo | GATCAAAACGAGAGGACAGC | SEQ ID NO: 81 |
| TRBV5aFi | CAGGGGCCCCAGTTTATCTT | SEQ ID NO: 82 |
| TRBV5bFi | GAAACARAGGAAACTTCCCT | SEQ ID NO: 83 |
| TRBV6aFo | GTGTGCCCAGGATATGAACC | SEQ ID NO: 84 |
| TRBV6bFo | CAGGATATGAGACATAATGC | SEQ ID NO: 85 |
| TRBV6aFi | GGTATCGACAAGACCCAGGC | SEQ ID NO: 86 |
| TRBV6bFi | TAGACAAGATCTAGGACTGG | SEQ ID NO: 87 |
| TRBV7Fo | CTCAGGTGTGATCCAATTTC | SEQ ID NO: 88 |

TABLE 1-continued

| Primer | Sequence | Sequence ID Number |
|---|---|---|
| TRBV7aFi | TCTAATTTACTTCCAAGGCA | SEQ ID NO: 89 |
| TRBV7bFi | TCCCAGAGTGATGCTCAACG | SEQ ID NO: 90 |
| TRBV7cFi | ACTTACTTCAATTATGAAGC | SEQ ID NO: 91 |
| TRBV7dFi | CCAGAATGAAGCTCAACTAG | SEQ ID NO: 92 |
| TRBV9Fo | GAGACCTCTCTGTGTACTGG | SEQ ID NO: 93 |
| TRBV9Fi | CTCATTCAGTATTATAATGG | SEQ ID NO: 94 |
| TRBV10Fo | GGAATCACCCAGAGCCCAAG | SEQ ID NO: 95 |
| TRBV10Fi | GACATGGGCTGAGGCTGATC | SEQ ID NO: 96 |
| TRBV11Fo | CCTAAGGATCGATTTTCTGC | SEQ ID NO: 97 |
| TRBV11Fi | ACTCTCAAGATCCAGCCTGC | SEQ ID NO: 98 |
| TRBV12Fo | AGGTGACAGAGATGGGACAA | SEQ ID NO: 99 |
| TRBV12aFi | TGCAGGGACTGGAATTGCTG | SEQ ID NO: 100 |
| TRBV12bFi | GTACAGACAGACCATGATGC | SEQ ID NO: 101 |
| TRBV13Fo | CTATCCTATCCCTAGACACG | SEQ ID NO: 102 |
| TRBV13Fi | AAGATGCAGAGCGATAAAGG | SEQ ID NO: 103 |
| TRBV14Fo | AGATGTGACCCAATTTCTGG | SEQ ID NO: 104 |
| TRBV14Fi | AGTCTAAACAGGATGAGTCC | SEQ ID NO: 105 |
| TRBV15Fo | TCAGACTTTGAACCATAACG | SEQ ID NO: 106 |
| TRBV15Fi | AAAGATTTTAACAATGAAGC | SEQ ID NO: 107 |
| TRBV16Fo | TATTGTGCCCCAATAAAAGG | SEQ ID NO: 108 |
| TRBV16Fi | AATGTCTTTGATGAAACAGG | SEQ ID NO: 109 |
| TRBV17Fo | ATCCATCTTCTGGTCACATG | SEQ ID NO: 110 |
| TRBV17Fi | AACATTGCAGTTGATTCAGG | SEQ ID NO: 111 |
| TRBV18Fo | GCAGCCCAATGAAAGGACAC | SEQ ID NO: 112 |
| TRBV18Fi | AATATCATAGATGAGTCAGG | SEQ ID NO: 113 |
| TRBV19Fo | TGAACAGAATTTGAACCACG | SEQ ID NO: 114 |
| TRBV19Fi | TTTCAGAAAGGAGATATAGC | SEQ ID NO: 115 |
| TRBV20F0 | TCGAGTGCCGTTCCCTGGAC | SEQ ID NO: 116 |
| TRBV20Fi | GATGGCAACTTCCAATGAGG | SEQ ID NO: 117 |
| TRBV21Fo | GCAAAGATGGATTGTGTTCC | SEQ ID NO: 118 |
| TRBV21Fi | CGCTGGAAGAAGAGCTCAAG | SEQ ID NO: 119 |
| TRBV23Fo | CATTTGGTCAAAGGAAAAGG | SEQ ID NO: 120 |
| TRBV23Fi | GAATGAACAAGTTCTTCAAG | SEQ ID NO: 121 |
| TRBV24Fo | ATGCTGGAATGTTCTCAGAC | SEQ ID NO: 122 |
| TRBV24Fi | GTCAAAGATATAAACAAAGG | SEQ ID NO: 123 |
| TRBV25Fo | CTCTGGAATGTTCTCAAACC | SEQ ID NO: 124 |
| TRBV25Fi | TAATTCCACAGAGAAGGGAG | SEQ ID NO: 125 |
| TRBV26Fo | CCCAGAATATGAATCATGTT | SEQ ID NO: 126 |
| TRBV26Fi | ATTCACCTGGCACTGGGAGC | SEQ ID NO: 127 |
| TRBV27Fo | TTGTTCTCAGAATATGAACC | SEQ ID NO: 128 |
| TRBV27Fi | TGAGGTGACTGATAAGGGAG | SEQ ID NO: 129 |
| TRBV28Fo | ATGTGTCCAGGATATGGACC | SEQ ID NO: 130 |
| TRBV28Fi | AAAAGGAGATATTCCTGAGG | SEQ ID NO: 131 |
| TRBV29Fo | TCACCATGATGTTCTGGTAC | SEQ ID NO: 132 |
| TRBV29Fi | CTGGACAGAGCCTGACACTG | SEQ ID NO: 133 |
| TRBV30F0 | TGTGGAGGGAACATCAAACC | SEQ ID NO: 134 |
| TRBV30Fi | TTCTACTCCGTTGGTATTGG | SEQ ID NO: 135 |
| TRBCR0 | GTGTGGCCTTTTGGGTGTGG | SEQ ID NO: 136 |
| TRBCRi | TCTGATGGCTCAAACACAGC | SEQ ID NO: 137 |
| TRDV1Fo | TGTATGAAACAAGTTGGTGG | SEQ ID NO: 138 |
| TRDV1Fi | CAGAATGCAAAAGTGGTCG | SEQ ID NO: 139 |
| TRDV2Fo | ATGAAAGGAGAAGCGATCGG | SEQ ID NO: 140 |
| TRDV2Fi | TGGTTTCAAAGACAATTTCC | SEQ ID NO: 141 |
| TRDV3Fo | GACACTGTATATTCAAATCC | SEQ ID NO: 142 |
| TRDV3Fi | GCAGATTTTACTCAAGGACG | SEQ ID NO: 143 |
| TRDCR0 | AGACAAGCGACATTTGTTCC | SEQ ID NO: 144 |
| TRDCRi | ACGGATGGTTTGGTATGAGG | SEQ ID NO: 145 |
| TRGV1-5Fo | GGGTCATCTGCTGAAATCAC | SEQ ID NO: 146 |
| TRGV1-5, 8Fi | AGGAGGGGAAGGCCCCACAG | SEQ ID NO: 147 |
| TRGV8Fo | GGGTCATCAGCTGTAATCAC | SEQ ID NO: 148 |
| TRGV5pFi | AGGAGGGGAAGACCCCACAG | SEQ ID NO: 149 |
| TRGV9Fo | AGCCCGCCTGGAATGTGTGG | SEQ ID NO: 150 |
| TRGV9Fi | GCACTGTCAGAAAGGAATCC | SEQ ID NO: 151 |
| TRGV10Fo | AAGAAAAGTATTGACATACC | SEQ ID NO: 152 |
| TRGV10Fi | ATATTGTCTCAACAAAATCC | SEQ ID NO: 153 |
| TRGV11Fo | AGAGTGCCCACATATCTTGG | SEQ ID NO: 154 |
| TRGV11Fi | GCTCAAGATTGCTCAGGTGG | SEQ ID NO: 155 |
| TRGCRo | GGATCCCAGAATCGTGTTGC | SEQ ID NO: 156 |
| TRGCRi | GGTATGTTCCAGCCTTCTGG | SEQ ID NO: 157 |

TABLE 2

| Primer | Sequence | Sequence ID Number |
|---|---|---|
| IgHV1aFo | AGTGAAGGTCTCCTGCAAGG | SEQ ID NO: 158 |
| IgHV1bFo | AGTGAAGGTTTCCTGCAAGG | SEQ ID NO: 159 |
| IgHV1aFi | AGTTCCAGGGCAGAGTCAC | SEQ ID NO: 160 |

TABLE 2-continued

| Primer | Sequence | Sequence ID Number |
|---|---|---|
| IgHV1bFi | AGTTTCAGGGCAGGGTCAC | SEQ ID NO: 161 |
| IgHV1cFi | AGTTCCAGGAAAGAGTCAC | SEQ ID NO: 162 |
| IgHV1dFi | AATTCCAGGACAGAGTCAC | SEQ ID NO: 163 |
| IgHV2Fo | TCTCTGGGTTCTCACTCAGC | SEQ ID NO: 164 |
| IgHV2Fi | AAGGCCCTGGAGTGGCTTGC | SEQ ID NO: 165 |
| IgHV3aFo | TCCCTGAGACTCTCCTGTGC | SEQ ID NO: 166 |
| IgHV3bFo | CTCCTGTGCAGCCTCTGG | SEQ ID NO: 167 |
| IgHV3cFo | GGTCCCTGAGACTCTCCTGT | SEQ ID NO: 168 |
| IgHV3dFo | CTGAGACTCTCCTGTGTAGC | SEQ ID NO: 169 |
| IgHV3aFi | CTCCAGGGAAGGGGCTGG | SEQ ID NO: 170 |
| IgHV3bFi | GGCTCCAGGCAAGGGGCT | SEQ ID NO: 171 |
| IgHV3cFi | ACTGGGTCCGCCAGGCTCC | SEQ ID NO: 172 |
| IgHV3dFi | GAAGGGGCTGGAGTGGGT | SEQ ID NO: 173 |
| IgHV3eFi | AAAAGGTCTGGAGTGGGT | SEQ ID NO: 174 |
| IgHV4Fo | AGACCCTGTCCCTCACCTGC | SEQ ID NO: 175 |
| IgHV4Fi | AGGGVCTGGAGTGGATTGGG | SEQ ID NO: 176 |
| IgHV5Fo | GCGCCAGATGCCCGGGAAAG | SEQ ID NO: 177 |
| IgHV5Fi | GGCCASGTCACCATCTCAGC | SEQ ID NO: 178 |
| IgHV6Fo | CCGGGGACAGTGTCTCTAGC | SEQ ID NO: 179 |
| IgHV6Fi | GCCTTGAGTGGCTGGGAAGG | SEQ ID NO: 180 |
| IgHV7Fo | GTTTCCTGCAAGGCTTCTGG | SEQ ID NO: 181 |
| IgHV7Fi | GGCTTGAGTGGATGGGATGG | SEQ ID NO: 182 |
| IgHJRo | ACCTGAGGAGACGGTGACC | SEQ ID NO: 183 |
| IgHJ1Ri | CAGTGCTGGAAGTATTCAGC | SEQ ID NO: 184 |
| IgHJ2Ri | AGAGATCGAAGTACCAGTAG | SEQ ID NO: 185 |
| IgHJ3Ri | CCCCAGATATCAAAAGCATC | SEQ ID NO: 186 |
| IgHJ4Ri | GGCCCCAGTAGTCAAAGTAG | SEQ ID NO: 187 |
| IgHJ5Ri | CCCAGGGGTCGAACCAGTTG | SEQ ID NO: 188 |
| IgHJ6Ri | CCCAGACGTCCATGTAGTAG | SEQ ID NO: 189 |
| IgKV1Fo | TAGGAGACAGAGTCACCATC | SEQ ID NO: 190 |
| IgKV1Fi | TTCAGYGRCAGTGGATCTGG | SEQ ID NO: 191 |
| IgKV2Fo | GGAGAGCCGGCCTCCATCTC | SEQ ID NO: 192 |
| IgKV2aFi | TGGTACCTGCAGAAGCCAGG | SEQ ID NO: 193 |
| IgKV2bFi | CTTCAGCAGAGGCCAGGCCA | SEQ ID NO: 194 |
| IgKV3-7Fo | GCCTGGTACCAGCAGAAACC | SEQ ID NO: 195 |
| IgKV3Fi | GCCAGGTTCAGTGGCAGTGG | SEQ ID NO: 196 |
| IgKV6-7Fi | TCGAGGTTCAGTGGCAGTGG | SEQ ID NO: 197 |
| IgKV4-5Fi | GACCGATTCAGTGGCAGCGG | SEQ ID NO: 198 |

TABLE 2-continued

| Primer | Sequence | Sequence ID Number |
|---|---|---|
| IgKCRo | TTCAACTGCTCATCAGATGG | SEQ ID NO: 199 |
| IgKCRi | ATGAAGACAGATGGTGCAGC | SEQ ID NO: 200 |
| IgLV1aFo | GGGCAGAGGGTCACCATCTC | SEQ ID NO: 201 |
| IgLV1bFo | GGACAGAAGGTCACCATCTC | SEQ ID NO: 202 |
| IgLV1aFi | TGGTACCAGCAGCTCCCAGG | SEQ ID NO: 203 |
| IgLV1bFi | TGGTACCAGCAGCTTCCAGG | SEQ ID NO: 204 |
| IgLV2Fo | CTGCACTGGAACCAGCAGTG | SEQ ID NO: 205 |
| IgLV2Fi | TCTCTGGCTCCAAGTCTGGC | SEQ ID NO: 206 |
| IgLV3aFo | ACCAGCAGAAGCCAGGCCAG | SEQ ID NO: 207 |
| IgLV3bFo | GAAGCCAGGACAGGCCCCTG | SEQ ID NO: 208 |
| IgLV3aFi | CTGAGCGATTCTCTGGCTCC | SEQ ID NO: 209 |
| IgLV3bFi | TTCTCTGGGTCCACCTCAGG | SEQ ID NO: 210 |
| IgLV3cFi | TTCTCTGGCTCCAGCTCAGG | SEQ ID NO: 211 |
| IgLV4Fo | TCGGTCAAGCTCACCTGCAC | SEQ ID NO: 212 |
| IgLV4Fi | GGGCTGACCGCTACCTCACC | SEQ ID NO: 213 |
| IgLV5Fo | CAGCCTGTGCTGACTCAGCC | SEQ ID NO: 214 |
| IgLV5Fi | CCAGCCGCTTCTCTGGATCC | SEQ ID NO: 215 |
| IgLV6Fo | CCATCTCCTGCACCCGCAGC | SEQ ID NO: 216 |
| IgLV7-8Fo | TCCCCWGGAGGGACAGTCAC | SEQ ID NO: 217 |
| IgLV9, 11Fo | CTCMCCTGCACCCTGAGCAG | SEQ ID NO: 218 |
| IgLV10Fo | AGACCGCCACACTCACCTGC | SEQ ID NO: 219 |
| IgLV6, 8Fi | CTGATCGSTTCTCTGGCTCC | SEQ ID NO: 220 |
| IgLV7Fi | CTGCCCGGTTCTCAGGCTCC | SEQ ID NO: 221 |
| IgLV9Fi | ATCCAGGAAGAGGATGAGAG | SEQ ID NO: 222 |
| IgLV10-11Fi | CTCCAGCCTGAGGACGAGGC | SEQ ID NO: 223 |
| IgLC1-7Ro | GCTCCCGGGTAGAAGTCACT | SEQ ID NO: 224 |
| IgLC1-7Ri | AGTGTGGCCTTGTTGGCTTG | SEQ ID NO: 225 |

TABLE 3

| Primer | Sequence | Sequence ID Number |
|---|---|---|
| HLAI Fo11 | CCCACTCCATGAGGTATTTC | SEQ ID NO: 226 |
| HLAI Fo12 | CCTACTCCATGAGGTATTTC | SEQ ID NO: 227 |
| HLAI Fo31 | GCGGGGAGCCCCGCTTCATC | SEQ ID NO: 228 |
| HLAI Fo32 | GCGGGAAGCCCCGCTTCATC | SEQ ID NO: 229 |

TABLE 3-continued

| Primer | Sequence | Sequence ID Number |
|---|---|---|
| HLAI Fo33 | GTGGAGAGCCCCGCTTCATC | SEQ ID NO: 230 |
| HLAI Fo34 | GCGGAAAGCCCCGCTTCATC | SEQ ID NO: 231 |
| HLAI Fo35 | GCGGAAAGCCCCACTTCATC | SEQ ID NO: 232 |
| HLAI Fo36 | GCGGGAAGCCCCACTTCATC | SEQ ID NO: 233 |
| HLAI Fi11 | GTGGGCTACGTGGACGACAC | SEQ ID NO: 234 |
| HLAI Fi12 | GTGGGCTACGTGGACGGCAC | SEQ ID NO: 235 |
| HLAI-Fi21 | GTTCGTGCGGTTCGACAGCG | SEQ ID NO: 236 |
| HLAI-Fi22 | GTTCGTGCGGTTTGACAGCG | SEQ ID NO: 237 |
| HLAI-Fi23 | GTTCGTGAGGTTCGACAGCG | SEQ ID NO: 238 |
| HLAI Ri11 | TAATCCTTGCCGTCGTAGGC | SEQ ID NO: 239 |
| HLAI Ri12 | TAATCCTTGCCGTCGTAAGC | SEQ ID NO: 240 |
| HLAI Ri13 | TAATCTTTGCCGTCGTAGGC | SEQ ID NO: 241 |
| HLAI Ro11 | GGTCCTCGTTCAGGGCGATG | SEQ ID NO: 242 |
| HLAI Ro12 | GGTCCTCTTTCAGGGCGATG | SEQ ID NO: 243 |
| HLAI Ro13 | GGTCCTCGTTCAAGGCGATG | SEQ ID NO: 244 |
| HLAI Ro14 | GATCCTCGTTCAGGGCGATG | SEQ ID NO: 245 |
| HLAI Ro15 | GGTCCTCATTCAGGGCGATG | SEQ ID NO: 246 |
| HLAI-Fo41 | GCCTACGACGGCAAGGATTA | SEQ ID NO: 247 |
| HLAI-Fo42 | GCTTACGACGGCAAGGATTA | SEQ ID NO: 248 |
| HLAI-Fo43 | GCCTACGACGGCAAAGATTA | SEQ ID NO: 249 |
| HLAI-Fi31 | CATCGCCCTGAACGAGGACC | SEQ ID NO: 250 |
| HLAI-Fi32 | CATCGCCCTGAAAGAGGACC | SEQ ID NO: 251 |
| HLAI-Fi33 | CATCGCCTTGAACGAGGACC | SEQ ID NO: 252 |
| HLAI-Fi34 | CATCGCCCTGAACGAGGATC | SEQ ID NO: 253 |
| HLAI-Fi35 | CATCGCCCTGAATGAGGACC | SEQ ID NO: 254 |
| HLAI-Ri21 | GGTATCTGCGGAGCCCGTCC | SEQ ID NO: 255 |
| HLAI-Ri22 | GGTATCTGCGGAGCCACTCC | SEQ ID NO: 256 |
| HLAI-Ri23 | GGTGTCTGCGGAGCCACTCC | SEQ ID NO: 257 |
| HLAI-Ri24 | GGTATCCGCGGAGCCACTCC | SEQ ID NO: 258 |
| HLAI-Ro21 | GCAGCGTCTCCTTCCCGTTC | SEQ ID NO: 259 |
| HLAI-Ro22 | CCAGCTTGTCCTTCCCGTTC | SEQ ID NO: 260 |
| HLAI-Ro23 | CCAGCGTGTCCTTCCCGTTC | SEQ ID NO: 261 |
| HLAI-Ro24 | GCAGCGTCTCCTTCCCATTC | SEQ ID NO: 262 |
| HLAI-Ro25 | GCAGCGTCTCCTTCCKGTTC | SEQ ID NO: 263 |
| DRB17 Fo11 | TGTCATTTCTTCAATGGGAC | SEQ ID NO: 264 |
| DRB1 Fo12 | AGTGTCATTTCTTCAACGGG | SEQ ID NO: 265 |
| DRB1 Fo13 | GTGTTATTTCTTCAATGGGA | SEQ ID NO: 266 |
| DRB1 Fo14 | GTGTCAATTCTTCAATGGGA | SEQ ID NO: 267 |
| DRB4 Fo | GTGTCATTTCCTCAATGGGA | SEQ ID NO: 268 |
| DRB1 Fi11 | GGAGCGGGTGCGGTTGCTGG | SEQ ID NO: 269 |
| DRB1 Fi12 | GGAGCGGGTGCGGTACCTGG | SEQ ID NO: 270 |
| DRB1 Fi13 | GGAGCGGGTGCGGTTCCTGG | SEQ ID NO: 271 |
| DRB1 Fi14 | GGAGCGGGTGCGATTCCTGG | SEQ ID NO: 272 |
| DRB1 Fi15 | GGAGCGGGTGCGGTATCTGC | SEQ ID NO: 273 |
| DRB1 Fi16 | GGAGCGGGTGCGGTTACTGG | SEQ ID NO: 274 |
| DRB45 Fi | ACATCTATAACCAAGAGGAG | SEQ ID NO: 275 |
| DRB6 Fi | ACATCCATAAACGGGAGGAG | SEQ ID NO: 276 |
| DRB7 Fi | TATAACCAAGAGGAGTACGT | SEQ ID NO: 277 |
| DRB Ri11 | AACCCCGTAGTTGTGTCTGC | SEQ ID NO: 278 |
| DRB4 Ri | AACCCCGTAGTTGTGTCTGC | SEQ ID NO: 279 |
| DRB6 Ri | CGTAATTGTATCTGCAGTAG | SEQ ID NO: 280 |
| DRB7 Ri | TAGTTGTCCACTTCGGCCCG | SEQ ID NO: 281 |
| DRB Ro1 | CGCTGCACTGTGAAGCTCTC | SEQ ID NO: 282 |
| DRB Ro2 | CGCTGCACCGTGAAGCTCTC | SEQ ID NO: 283 |

TABLE 3-continued

| Primer | Sequence | Sequence ID Number |
|---|---|---|
| DRA Fo | CCTGTGGAACTGAGAGAGCC | SEQ ID NO: 284 |
| DRA Fi | CAACGTCCTCATCTGTTTCA | SEQ ID NO: 285 |
| DRA Ri | CTGCTGCATTGCTTTTGCGC | SEQ ID NO: 286 |
| DRA Ro | TTACAGAGGCCCCCTGCGTT | SEQ ID NO: 287 |
| DPB Fo | GTCCAGGGCAGGGCCACTCC | SEQ ID NO: 288 |
| DPB Fi11 | AATTACGTGTACCAGGGACG | SEQ ID NO: 289 |
| DPB Fi12 | AATTACCTTTTCCAGGGACG | SEQ ID NO: 290 |
| DPB Fi13 | AATTACGTGTACCAGTTACG | SEQ ID NO: 291 |
| DPB Fi14 | AATTACGCGTACCAGTTACG | SEQ ID NO: 292 |
| DPB Ri11 | CGGCCTCGTCCAGCTCGTAG | SEQ ID NO: 293 |
| DPB Ri12 | TGGGCCCGCCCAGCTCGTAG | SEQ ID NO: 294 |
| DPB Ri13 | TGGGCCCGACCAGCTCGTAG | SEQ ID NO: 295 |
| DPB Ro | GGACTCGGCGCTGCAGGGTC | SEQ ID NO: 296 |
| DPA Fo | AGGAGCTGGGGCCATCAAGG | SEQ ID NO: 297 |
| DPA Fi | GACCATGTGTCAACTTATGC | SEQ ID NO: 298 |
| DPA Ri1 | CTCAGGGGGATCGTTGGTGG | SEQ ID NO: 299 |
| DPA Ri2 | CTCAGGGGGATCATTGGCGG | SEQ ID NO: 300 |
| DPA Ro | CAGCTCCACAGGCTCCTTGG | SEQ ID NO: 301 |
| DQB Fo | ACTCTCCCGAGGATTTCGTG | SEQ ID NO: 302 |
| DQB Fi | TGTGCTACTTCACCAACGGG | SEQ ID NO: 303 |
| DQB Ri1 | ACCTCGTAGTTGTGTCTGCA | SEQ ID NO: 304 |
| DQB Ri2 | AACTGGTAGTTGTGTCTGCA | SEQ ID NO: 305 |
| DQB Ro1 | ACTCTCCTCTGCAGGATCCC | SEQ ID NO: 306 |
| DQB Ro2 | ACTCGCCGCTGCAAGGTCGT | SEQ ID NO: 307 |
| DQB Ro3 | ACTCTCCTCTGCAAGATCCC | SEQ ID NO: 308 |
| DQA Fo | TGGTGTAAACTTGTACCAGT | SEQ ID NO: 309 |
| DQA Fi | ACCCATGAATTTGATGGAGA | SEQ ID NO: 310 |
| DQA Ri | GGAACCTCATTGGTAGCAGC | SEQ ID NO: 311 |
| DQA Ro | ACTTGGAAAACACTGTGACC | SEQ ID NO: 312 |

What is claimed is:

1. A method comprising:
   (a) selecting at least 2 V gene segment primers;
   (b) selecting at least 2 J gene segment primers;
   (c) combining the V gene segment and J gene segment primers with genomic DNA comprising rearranged nucleic acid molecules of a TCR region from lymphocytes obtained from a human or animal subject;
   (d) amplifying, in one reaction, said rearranged nucleic acid molecules from said sample using said V gene segment and J gene segment primers in a first amplification reaction, thereby producing non-identical amplicons sufficient to evaluate an immune response, the non-identical amplicons representing a diversity of TCR genes;
   wherein each of said at least 2 V gene segment primers is capable of annealing to V gene segment sequence and amplifying V gene segment sequence, and each of said at least 2 J gene segment primers is capable of annealing to J gene segment sequence and amplifying J gene segment sequence,
   wherein each of said V gene segment primers comprises a first sequence and a second sequence, wherein said first sequence is complementary to a portion of at least one V gene segment, wherein said second sequence contains a binding site for a common primer, and
   wherein each of said J gene segment primers comprises a first sequence and a second sequence, wherein said first sequence is complementary to a portion of a J gene segment, wherein said second sequence contains a binding site for a common primer;
   (e) rescuing the amplicons from the first amplification reaction by dilution of the amplicons and primers from the first amplification reaction; and
   (f) amplifying, in one reaction, the amplicons from the first amplification reaction in a second amplification reaction using at least one common primer which binds to the at least one common primer binding site and preserves the relative ratios of each amplicon from the first amplification reaction;
   wherein diluted primers from the first amplification reaction are present during the second amplification reaction.

2. The method of claim 1, wherein said first sequence of each V gene segment primer comprises a sequence that is complementary to a V Beta gene segment.

3. The method of claim 1, further comprising sequencing the amplicons.

4. The method of claim 3, wherein sequencing utilizes a set of primers that are complementary to a defined region within the amplicons.

5. The method of claim 4, further comprising quantifying non-identical DNA sequences representing T-cell receptor Beta rearrangements among the amplicons.

6. The method of claim 5, wherein the method allows amplification of the entire immunorepertoire of a human.

* * * * *

SEQUENCE LISTING

```
<160> NUMBER OF SEQ ID NOS: 312

<210> SEQ ID NO 1
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 1
tgcacgtacc agacatctgg                                                 20

<210> SEQ ID NO 2
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 2
aggtcgtttt tcttcattcc                                                 20

<210> SEQ ID NO 3
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
```

```
<222> LOCATION: (1)..(20)

<400> SEQUENCE: 3
tctgtaatca ctctgtgtcc                                          20

<210> SEQ ID NO 4
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 4
agggacgata caacatgacc                                          20

<210> SEQ ID NO 5
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 5
ctattcagtc tctggaaacc                                          20

<210> SEQ ID NO 6
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 6
atacatcaca ggggataacc                                          20

<210> SEQ ID NO 7
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 7
tgtagccaca acaacattgc                                          20

<210> SEQ ID NO 8
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 8
```
aaagttacaa acgaagtggc                                               20

<210> SEQ ID NO 9
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 9
gcacttacac agacagctcc                                               20

<210> SEQ ID NO 10
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 10
tatggacatg aaacaagacc                                               20

<210> SEQ ID NO 11
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 11
gcaactatac aaactattcc                                               20

<210> SEQ ID NO 12
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 12
gttttcttgc tactcatacg                                               20

<210> SEQ ID NO 13
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 13
tgcacgtact ctgtcagtcg                                               20

<210> SEQ ID NO 14

```
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 14
ggatatgaga agcagaaagg                                              20

<210> SEQ ID NO 15
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 15
ggatatgaga agcagaaagg                                              20

<210> SEQ ID NO 16
<211> LENGTH: 19
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(19)

<400> SEQUENCE: 16
ggytttgagg ctgaattta                                               19

<210> SEQ ID NO 17
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 17
gtccaatatc ctggagaagg                                              20

<210> SEQ ID NO 18
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 18
aaccacttct ttccacttgg                                              20

<210> SEQ ID NO 19
<211> LENGTH: 20
<212> TYPE: DNA
<213> ORGANISM: Artificial Sequence
<220> FEATURE:
```

```
<223> OTHER INFORMATION: Primer for PCR amplification
<220> FEATURE:
<221> NAME/KEY: primer_bind
<222> LOCATION: (1)..(20)

<400> SEQUENCE: 19
aatgcaatta tacagtgagc                                              20

<210> SEQ ID NO 20
<211> LENGTH: 20
<212> TYPE: DNA
<213> ORGANISM: Artificial Sequence
<220> FEATURE:
<223> OTHER INFORMATION: Primer for PCR amplification

<400> SEQUENCE: 20
tgagaacaca aagtcgaacg                                              20

<210> SEQ ID NO 21
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 21
tcttaattgt acttatcagg                                              20

<210> SEQ ID NO 22
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 22
tcaatcaagc cagaaggagc                                              20

<210> SEQ ID NO 23
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 23
tcagtgttcc agagggagcc                                              20

<210> SEQ ID NO 24
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 24
```

```
atggaaggtt tacagcacag                                               20

<210> SEQ ID NO 25
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 25
accctgagtg tccaggaggg                                               20

<210> SEQ ID NO 26
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 26
ttatagacat tcgttcaaat                                               20

<210> SEQ ID NO 27
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 27
tggactgcac atatgacacc                                               20

<210> SEQ ID NO 28
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 28
cagcaaaatg caacagaagg                                               20

<210> SEQ ID NO 29
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 29
agctgaagtg caactattcc                                               20

<210> SEQ ID NO 30
```

```
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 30
tctagagaga gcatcaaagg                                          20

<210> SEQ ID NO 31
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 31
aatgccacca tgaactgcag                                          20

<210> SEQ ID NO 32
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 32
gaaagagaga aacacagtgg                                          20

<210> SEQ ID NO 33
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 33
gctctgacat taaactgcac                                          20

<210> SEQ ID NO 34
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 34
caggagacgg acagcagagg                                          20

<210> SEQ ID NO 35
<211> LENGTH: 20
<212> TYPE: DNA
<213> ORGANISM: Artificial Sequence
<220> FEATURE:
```

<223> OTHER INFORMATION: Primer for PCR amplification
<220> FEATURE:
<221> NAME/KEY: primer_bind
<222> LOCATION: (1)..(20)

<400> SEQUENCE: 35
atgtgacctt ggactgtgtg                                                     20

<210> SEQ ID NO 36
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 36
gagcaaaatg aaataagtgg                                                     20

<210> SEQ ID NO 37
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 37
actgcagtta cacagtcagc                                                     20

<210> SEQ ID NO 38
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 38
agaaagaaag gctaaaagcc                                                     20

<210> SEQ ID NO 39
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 39
actgcagttt cactgatagc                                                     20

<210> SEQ ID NO 40
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

-continued

```
<400> SEQUENCE: 40
caagtggaag acttaatgcc                                                    20

<210> SEQ ID NO 41
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 41
gggagccaat tccacgctgc                                                    20

<210> SEQ ID NO 42
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 42
atggaagatt aagcgccacg                                                    20

<210> SEQ ID NO 43
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 43
atttcaatta taaactgtgc                                                    20

<210> SEQ ID NO 44
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 44
aaggaagatt cacaatctcc                                                    20

<210> SEQ ID NO 45
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 45
gcaccaattt cacctgcagc                                                    20
```

<210> SEQ ID NO 46
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 46
aggacgaata agtgccactc                                               20

<210> SEQ ID NO 47
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 47
tcaccacgta ctgcaattcc                                               20

<210> SEQ ID NO 48
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 48
agactgacat ttcagtttgg                                               20

<210> SEQ ID NO 49
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 49
tcgacagatt cmctcccagg                                               20

<210> SEQ ID NO 50
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 50
gtccagyacc ttgatcctgc                                               20

<210> SEQ ID NO 51
<211> LENGTH: 20

```
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 51
cctcaagtgt tttttccagc                                                    20

<210> SEQ ID NO 52
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 52
gtgacagtag ttacgggtgg                                                    20

<210> SEQ ID NO 53
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 53
cagcatgttt gattatttcc                                                    20

<210> SEQ ID NO 54
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 54
ctccaaggct ttatattctg                                                    20

<210> SEQ ID NO 55
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 55
ctccaaggct ttatattctg                                                    20

<210> SEQ ID NO 56
<211> LENGTH: 20
<212> TYPE: DNA
<213> ORGANISM: Artificial Sequence
<220> FEATURE:
<223> OTHER INFORMATION: Primer for PCR amplification
```

```
<220> FEATURE:
<221> NAME/KEY: primer_bind
<222> LOCATION: (1)..(20)

<400> SEQUENCE: 56
atgatattac tgaagggtgg                                              20

<210> SEQ ID NO 57
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 57
actgcacgtc atcaaagacg                                              20

<210> SEQ ID NO 58
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 58
ttgatgatgc tacagaaagg                                              20

<210> SEQ ID NO 59
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 59
tgaactgcac ttcttcaagc                                              20

<210> SEQ ID NO 60
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 60
cttgatagcc ttatataagg                                              20

<210> SEQ ID NO 61
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)
```

<400> SEQUENCE: 61
tcaattgcag ttatgaagtg                                                    20

<210> SEQ ID NO 62
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 62
tttatgctaa cttcaagtgg                                                    20

<210> SEQ ID NO 63
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 63
gcacatatga caccagtgag                                                    20

<210> SEQ ID NO 64
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 64
tcgccaagaa gcttataagc                                                    20

<210> SEQ ID NO 65
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 65
tctactgcaa ttattcaacc                                                    20

<210> SEQ ID NO 66
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 66
caggagggac gattaatggc                                                    20

-continued

```
<210> SEQ ID NO 67
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 67
tgaactgcac atacacatcc                                               20

<210> SEQ ID NO 68
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 68
acagcaaaaa cttcggaggc                                               20

<210> SEQ ID NO 69
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 69
aactgcagtt actcggtagg                                               20

<210> SEQ ID NO 70
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 70
aagcatggaa gattaattgc                                               20

<210> SEQ ID NO 71
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 71
gcagacagac ttgtcactgg                                               20

<210> SEQ ID NO 72
<211> LENGTH: 20
<212> TYPE: DNA
```

```
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 72
agtctctcag ctggtacacg                                              20

<210> SEQ ID NO 73
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 73
aatgaaacgt gagcatctgg                                              20

<210> SEQ ID NO 74
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 74
cattgaaaac aagactgtgc                                              20

<210> SEQ ID NO 75
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 75
gtgtccccat ctctaatcac                                              20

<210> SEQ ID NO 76
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 76
tgaaatctca gagaagtctg                                              20

<210> SEQ ID NO 77
<211> LENGTH: 20
<212> TYPE: DNA
<213> ORGANISM: Artificial Sequence
<220> FEATURE:
<223> OTHER INFORMATION: Primer for PCR amplification
<220> FEATURE:
```

```
<221> NAME/KEY: primer_bind
<222> LOCATION: (1)..(20)

<400> SEQUENCE: 77
tatgtattgg tataaacagg                                            20

<210> SEQ ID NO 78
<211> LENGTH: 20
<212> TYPE: DNA
<213> ORGANISM: Artificial Sequence
<220> FEATURE:
<223> OTHER INFORMATION: Primer for PCR amplification

<400> SEQUENCE: 78
ctctaagaaa tttctgaaga                                            20

<210> SEQ ID NO 79
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 79
gtctttgaaa tgtgaacaac                                            20

<210> SEQ ID NO 80
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 80
ggagctcatg tttgtctaca                                            20

<210> SEQ ID NO 81
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 81
gatcaaaacg agaggacagc                                            20

<210> SEQ ID NO 82
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 82
caggggcccc agtttatctt                                            20
```

<210> SEQ ID NO 83
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 83
gaaacaragg aaacttccct                                                   20

<210> SEQ ID NO 84
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 84
gtgtgcccag gatatgaacc                                                   20

<210> SEQ ID NO 85
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 85
caggatatga gacataatgc                                                   20

<210> SEQ ID NO 86
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 86
ggtatcgaca agacccaggc                                                   20

<210> SEQ ID NO 87
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 87
tagacaagat ctaggactgg                                                   20

<210> SEQ ID NO 88
<211> LENGTH: 20
<212> TYPE: DNA

<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 88
ctcaggtgtg atccaatttc        20

<210> SEQ ID NO 89
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 89
tctaatttac ttccaaggca        20

<210> SEQ ID NO 90
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 90
tcccagagtg atgctcaacg        20

<210> SEQ ID NO 91
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 91
acttacttca attatgaagc        20

<210> SEQ ID NO 92
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 92
ccagaatgaa gctcaactag        20

<210> SEQ ID NO 93
<211> LENGTH: 20
<212> TYPE: DNA
<213> ORGANISM: Artificial Sequence
<220> FEATURE:
<223> OTHER INFORMATION: Primer for PCR amplification
<220> FEATURE:

```
<221> NAME/KEY: primer_bind
<222> LOCATION: (1)..(20)

<400> SEQUENCE: 93
gagacctctc tgtgtactgg                                               20

<210> SEQ ID NO 94
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 94
ctcattcagt attataatgg                                               20

<210> SEQ ID NO 95
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 95
ggaatcaccc agagcccaag                                               20

<210> SEQ ID NO 96
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 96
gacatgggct gaggctgatc                                               20

<210> SEQ ID NO 97
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 97
cctaaggatc gattttctgc                                               20

<210> SEQ ID NO 98
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 98
```
actctcaaga tccagcctgc                                              20

<210> SEQ ID NO 99
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 99
aggtgacaga gatgggacaa                                              20

<210> SEQ ID NO 100
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 100
tgcagggact ggaattgctg                                              20

<210> SEQ ID NO 101
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 101
gtacagacag accatgatgc                                              20

<210> SEQ ID NO 102
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 102
ctatcctatc cctagacacg                                              20

<210> SEQ ID NO 103
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 103
aagatgcaga gcgataaagg                                              20

-continued

```
<210> SEQ ID NO 104
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 104
agatgtgacc caatttctgg                                               20

<210> SEQ ID NO 105
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 105
agtctaaaca ggatgagtcc                                               20

<210> SEQ ID NO 106
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 106
tcagactttg aaccataacg                                               20

<210> SEQ ID NO 107
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 107
aaagatttta acaatgaagc                                               20

<210> SEQ ID NO 108
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 108
tattgtgccc caataaaagg                                               20

<210> SEQ ID NO 109
<211> LENGTH: 20
<212> TYPE: DNA
<213> ORGANISM: Artificial Sequence
```

```
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 109
aatgtctttg atgaaacagg                                          20

<210> SEQ ID NO 110
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 110
atccatcttc tggtcacatg                                          20

<210> SEQ ID NO 111
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 111
aacattgcag ttgattcagg                                          20

<210> SEQ ID NO 112
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 112
gcagcccaat gaaaggacac                                          20

<210> SEQ ID NO 113
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 113
aatatcatag atgagtcagg                                          20

<210> SEQ ID NO 114
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
```

```
<222> LOCATION: (1)..(20)

<400> SEQUENCE: 114
tgaacagaat ttgaaccacg                                               20

<210> SEQ ID NO 115
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 115
tttcagaaag gagatatagc                                               20

<210> SEQ ID NO 116
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 116
tcgagtgccg ttccctggac                                               20

<210> SEQ ID NO 117
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 117
gatggcaact tccaatgagg                                               20

<210> SEQ ID NO 118
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 118
gcaaagatgg attgtgttcc                                               20

<210> SEQ ID NO 119
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 119
```
cgctggaaga agagctcaag                                              20

<210> SEQ ID NO 120
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 120
catttggtca aaggaaaagg                                              20

<210> SEQ ID NO 121
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 121
gaatgaacaa gttcttcaag                                              20

<210> SEQ ID NO 122
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 122
atgctggaat gttctcagac                                              20

<210> SEQ ID NO 123
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 123
gtcaaagata taaacaaagg                                              20

<210> SEQ ID NO 124
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 124
ctctggaatg ttctcaaacc                                              20

<210> SEQ ID NO 125

```
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 125
taattccaca gagaagggag                                               20

<210> SEQ ID NO 126
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 126
cccagaatat gaatcatgtt                                               20

<210> SEQ ID NO 127
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 127
attcacctgg cactgggagc                                               20

<210> SEQ ID NO 128
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 128
ttgttctcag aatatgaacc                                               20

<210> SEQ ID NO 129
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 129
tgaggtgact gataagggag                                               20

<210> SEQ ID NO 130
<211> LENGTH: 20
<212> TYPE: DNA
<213> ORGANISM: Artificial Sequence
<220> FEATURE:
```

<223> OTHER INFORMATION: Primer for PCR amplification
<220> FEATURE:
<221> NAME/KEY: primer_bind
<222> LOCATION: (1)..(20)

<400> SEQUENCE: 130
atgtgtccag gatatggacc                                              20

<210> SEQ ID NO 131
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 131
aaaaggagat attcctgagg                                              20

<210> SEQ ID NO 132
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 132
tcaccatgat gttctggtac                                              20

<210> SEQ ID NO 133
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 133
ctggacagag cctgacactg                                              20

<210> SEQ ID NO 134
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 134
tgtggaggga acatcaaacc                                              20

<210> SEQ ID NO 135
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

```
<400> SEQUENCE: 135
ttctactccg ttggtattgg                                                    20

<210> SEQ ID NO 136
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 136
gtgtggcctt ttgggtgtgg                                                    20

<210> SEQ ID NO 137
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 137
tctgatggct caaacacagc                                                    20

<210> SEQ ID NO 138
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 138
tgtatgaaac aagttggtgg                                                    20

<210> SEQ ID NO 139
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 139
cagaatgcaa aaagtggtcg                                                    20

<210> SEQ ID NO 140
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 140
atgaaaggag aagcgatcgg                                                    20
```

<210> SEQ ID NO 141
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 141
tggtttcaaa gacaatttcc                                          20

<210> SEQ ID NO 142
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 142
gacactgtat attcaaatcc                                          20

<210> SEQ ID NO 143
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 143
gcagatttta ctcaaggacg                                          20

<210> SEQ ID NO 144
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 144
agacaagcga catttgttcc                                          20

<210> SEQ ID NO 145
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 145
acggatggtt tggtatgagg                                          20

<210> SEQ ID NO 146
<211> LENGTH: 20

```
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 146
gggtcatctg ctgaaatcac                                          20

<210> SEQ ID NO 147
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 147
aggaggggaa ggccccacag                                          20

<210> SEQ ID NO 148
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 148
gggtcatcag ctgtaatcac                                          20

<210> SEQ ID NO 149
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 149
aggaggggaa gaccccacag                                          20

<210> SEQ ID NO 150
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 150
agcccgcctg gaatgtgtgg                                          20

<210> SEQ ID NO 151
<211> LENGTH: 20
<212> TYPE: DNA
<213> ORGANISM: Artificial Sequence
<220> FEATURE:
<223> OTHER INFORMATION: Primer for PCR amplification
```

-continued

```
<220> FEATURE:
<221> NAME/KEY: primer_bind
<222> LOCATION: (1)..(20)

<400> SEQUENCE: 151
gcactgtcag aaaggaatcc                                                20

<210> SEQ ID NO 152
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 152
aagaaaagta ttgacatacc                                                20

<210> SEQ ID NO 153
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 153
atattgtctc aacaaaatcc                                                20

<210> SEQ ID NO 154
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 154
agagtgccca catatcttgg                                                20

<210> SEQ ID NO 155
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 155
gctcaagatt gctcaggtgg                                                20

<210> SEQ ID NO 156
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)
```

-continued

<400> SEQUENCE: 156
ggatcccaga atcgtgttgc                                               20

<210> SEQ ID NO 157
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 157
ggtatgttcc agccttctgg                                               20

<210> SEQ ID NO 158
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 158
agtgaaggtc tcctgcaagg                                               20

<210> SEQ ID NO 159
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 159
agtgaaggtt tcctgcaagg                                               20

<210> SEQ ID NO 160
<211> LENGTH: 19
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(19)

<400> SEQUENCE: 160
agttccaggg cagagtcac                                                19

<210> SEQ ID NO 161
<211> LENGTH: 19
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(19)

<400> SEQUENCE: 161
agtttcaggg cagggtcac                                                19

```
<210> SEQ ID NO 162
<211> LENGTH: 19
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(19)

<400> SEQUENCE: 162
agttccagga aagagtcac                                               19

<210> SEQ ID NO 163
<211> LENGTH: 19
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(19)

<400> SEQUENCE: 163
aattccagga cagagtcac                                               19

<210> SEQ ID NO 164
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 164
tctctgggtt ctcactcagc                                              20

<210> SEQ ID NO 165
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 165
aaggccctgg agtggcttgc                                              20

<210> SEQ ID NO 166
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 166
tccctgagac tctcctgtgc                                              20

<210> SEQ ID NO 167
<211> LENGTH: 20
<212> TYPE: DNA
```

<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 167
ctctcctgtg cagcctctgg                                        20

<210> SEQ ID NO 168
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 168
ggtccctgag actctcctgt                                        20

<210> SEQ ID NO 169
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 169
ctgagactct cctgtgtagc                                        20

<210> SEQ ID NO 170
<211> LENGTH: 18
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(18)

<400> SEQUENCE: 170
ctccagggaa ggggctgg                                          18

<210> SEQ ID NO 171
<211> LENGTH: 18
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(18)

<400> SEQUENCE: 171
ggctccaggc aagggggct                                         18

<210> SEQ ID NO 172
<211> LENGTH: 19
<212> TYPE: DNA
<213> ORGANISM: Artificial Sequence
<220> FEATURE:
<223> OTHER INFORMATION: Primer for PCR amplification
<220> FEATURE:

```
<221> NAME/KEY: primer_bind
<222> LOCATION: (1)..(19)

<400> SEQUENCE: 172
actgggtccg ccaggctcc                                                    19

<210> SEQ ID NO 173
<211> LENGTH: 18
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(18)

<400> SEQUENCE: 173
gaaggggctg gagtgggt                                                     18

<210> SEQ ID NO 174
<211> LENGTH: 18
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(18)

<400> SEQUENCE: 174
aaaaggtctg gagtgggt                                                     18

<210> SEQ ID NO 175
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 175
agaccctgtc cctcacctgc                                                   20

<210> SEQ ID NO 176
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 176
agggvctgga gtggattggg                                                   20

<210> SEQ ID NO 177
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 177
```
gcgccagatg cccgggaaag                                              20

<210> SEQ ID NO 178
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 178
ggccasgtca ccatctcagc                                              20

<210> SEQ ID NO 179
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 179
ccggggacag tgtctctagc                                              20

<210> SEQ ID NO 180
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 180
gccttgagtg gctgggaagg                                              20

<210> SEQ ID NO 181
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 181
gtttcctgca aggcttctgg                                              20

<210> SEQ ID NO 182
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 182
ggcttgagtg gatgggatgg                                              20

```
<210> SEQ ID NO 183
<211> LENGTH: 19
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(19)

<400> SEQUENCE: 183
acctgaggag acggtgacc                                                  19

<210> SEQ ID NO 184
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 184
cagtgctgga agtattcagc                                                 20

<210> SEQ ID NO 185
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 185
agagatcgaa gtaccagtag                                                 20

<210> SEQ ID NO 186
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 186
ccccagatat caaaagcatc                                                 20

<210> SEQ ID NO 187
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 187
ggccccagta gtcaaagtag                                                 20

<210> SEQ ID NO 188
<211> LENGTH: 20
<212> TYPE: DNA
<213> ORGANISM: Artificial Sequence
```

```
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 188
cccaggggtc gaaccagttg                                               20

<210> SEQ ID NO 189
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 189
cccagacgtc catgtagtag                                               20

<210> SEQ ID NO 190
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 190
taggagacag agtcaccatc                                               20

<210> SEQ ID NO 191
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 191
ttcagygrca gtggatctgg                                               20

<210> SEQ ID NO 192
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 192
ggagagccgg cctccatctc                                               20

<210> SEQ ID NO 193
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
```

```
<222> LOCATION: (1)..(20)

<400> SEQUENCE: 193
tggtacctgc agaagccagg                                                    20

<210> SEQ ID NO 194
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 194
cttcagcaga ggccaggcca                                                    20

<210> SEQ ID NO 195
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 195
gcctggtacc agcagaaacc                                                    20

<210> SEQ ID NO 196
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 196
gccaggttca gtggcagtgg                                                    20

<210> SEQ ID NO 197
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 197
tcgaggttca gtggcagtgg                                                    20

<210> SEQ ID NO 198
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 198
```

```
gaccgattca gtggcagcgg                                               20

<210> SEQ ID NO 199
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 199
ttcaactgct catcagatgg                                               20

<210> SEQ ID NO 200
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 200
atgaagacag atggtgcagc                                               20

<210> SEQ ID NO 201
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 201
gggcagaggg tcaccatctc                                               20

<210> SEQ ID NO 202
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 202
ggacagaagg tcaccatctc                                               20

<210> SEQ ID NO 203
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 203
tggtaccagc agctcccagg                                               20

<210> SEQ ID NO 204
```

<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 204
tggtaccagc agcttccagg                                          20

<210> SEQ ID NO 205
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 205
ctgcactgga accagcagtg                                          20

<210> SEQ ID NO 206
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 206
tctctggctc caagtctggc                                          20

<210> SEQ ID NO 207
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 207
accagcagaa gccaggccag                                          20

<210> SEQ ID NO 208
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 208
gaagccagga caggcccctg                                          20

<210> SEQ ID NO 209
<211> LENGTH: 20
<212> TYPE: DNA
<213> ORGANISM: Artificial Sequence
<220> FEATURE:

```
<223> OTHER INFORMATION: Primer for PCR amplification
<220> FEATURE:
<221> NAME/KEY: primer_bind
<222> LOCATION: (1)..(20)

<400> SEQUENCE: 209
ctgagcgatt ctctggctcc                                               20

<210> SEQ ID NO 210
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 210
ttctctgggt ccacctcagg                                               20

<210> SEQ ID NO 211
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 211
ttctctggct ccagctcagg                                               20

<210> SEQ ID NO 212
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 212
tcggtcaagc tcacctgcac                                               20

<210> SEQ ID NO 213
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 213
gggctgaccg ctacctcacc                                               20

<210> SEQ ID NO 214
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)
```

```
<400> SEQUENCE: 214
cagcctgtgc tgactcagcc                                               20

<210> SEQ ID NO 215
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 215
ccagccgctt ctctggatcc                                               20

<210> SEQ ID NO 216
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 216
ccatctcctg cacccgcagc                                               20

<210> SEQ ID NO 217
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 217
tccccwggag ggacagtcac                                               20

<210> SEQ ID NO 218
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 218
ctcmcctgca ccctgagcag                                               20

<210> SEQ ID NO 219
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 219
agaccgccac actcacctgc                                               20
```

```
<210> SEQ ID NO 220
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 220
ctgatcgstt ctctggctcc                                          20

<210> SEQ ID NO 221
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 221
ctgcccggtt ctcaggctcc                                          20

<210> SEQ ID NO 222
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 222
atccaggaag aggatgagag                                          20

<210> SEQ ID NO 223
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 223
ctccagcctg aggacgaggc                                          20

<210> SEQ ID NO 224
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 224
gctcccgggt agaagtcact                                          20

<210> SEQ ID NO 225
<211> LENGTH: 20
```

```
-continued

<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 225
agtgtggcct tgttggcttg                                        20

<210> SEQ ID NO 226
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 226
cccactccat gaggtatttc                                        20

<210> SEQ ID NO 227
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 227
cctactccat gaggtatttc                                        20

<210> SEQ ID NO 228
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 228
gcggggagcc ccgcttcatc                                        20

<210> SEQ ID NO 229
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 229
gcgggaagcc ccgcttcatc                                        20

<210> SEQ ID NO 230
<211> LENGTH: 20
<212> TYPE: DNA
<213> ORGANISM: Artificial Sequence
<220> FEATURE:
<223> OTHER INFORMATION: Primer for PCR amplification
```

```
<220> FEATURE:
<221> NAME/KEY: primer_bind
<222> LOCATION: (1)..(20)

<400> SEQUENCE: 230
gtggagagcc ccgcttcatc                                                    20

<210> SEQ ID NO 231
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 231
gcggaaagcc ccgcttcatc                                                    20

<210> SEQ ID NO 232
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 232
gcggaaagcc ccacttcatc                                                    20

<210> SEQ ID NO 233
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 233
gcgggaagcc ccacttcatc                                                    20

<210> SEQ ID NO 234
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 234
gtgggctacg tggacgacac                                                    20

<210> SEQ ID NO 235
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)
```

```
<400> SEQUENCE: 235
gtgggctacg tggacggcac                                               20

<210> SEQ ID NO 236
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 236
gttcgtgcgg ttcgacagcg                                               20

<210> SEQ ID NO 237
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 237
gttcgtgcgg tttgacagcg                                               20

<210> SEQ ID NO 238
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 238
gttcgtgagg ttcgacagcg                                               20

<210> SEQ ID NO 239
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 239
taatccttgc cgtcgtaggc                                               20

<210> SEQ ID NO 240
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 240
taatccttgc cgtcgtaagc                                               20
```

<210> SEQ ID NO 241
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 241
taatctttgc cgtcgtaggc        20

<210> SEQ ID NO 242
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 242
ggtcctcgtt cagggcgatg        20

<210> SEQ ID NO 243
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 243
ggtcctcttt cagggcgatg        20

<210> SEQ ID NO 244
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 244
ggtcctcgtt caaggcgatg        20

<210> SEQ ID NO 245
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 245
gatcctcgtt cagggcgatg        20

<210> SEQ ID NO 246
<211> LENGTH: 20
<212> TYPE: DNA

<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 246
ggtcctcatt cagggcgatg                                          20

<210> SEQ ID NO 247
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 247
gcctacgacg gcaaggatta                                          20

<210> SEQ ID NO 248
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 248
gcttacgacg gcaaggatta                                          20

<210> SEQ ID NO 249
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 249
gcctacgacg gcaaagatta                                          20

<210> SEQ ID NO 250
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 250
catcgccctg aacgaggacc                                          20

<210> SEQ ID NO 251
<211> LENGTH: 20
<212> TYPE: DNA
<213> ORGANISM: Artificial Sequence
<220> FEATURE:
<223> OTHER INFORMATION: Primer for PCR amplification
<220> FEATURE:

```
<221> NAME/KEY: primer_bind
<222> LOCATION: (1)..(20)

<400> SEQUENCE: 251
catcgccctg aaagaggacc                                               20

<210> SEQ ID NO 252
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 252
catcgccttg aacgaggacc                                               20

<210> SEQ ID NO 253
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 253
catcgccctg aacgaggatc                                               20

<210> SEQ ID NO 254
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 254
catcgccctg aatgaggacc                                               20

<210> SEQ ID NO 255
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 255
ggtatctgcg gagcccgtcc                                               20

<210> SEQ ID NO 256
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 256
```
ggtatctgcg gagccactcc                                                   20

<210> SEQ ID NO 257
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 257
ggtgtctgcg gagccactcc                                                   20

<210> SEQ ID NO 258
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 258
ggtatccgcg gagccactcc                                                   20

<210> SEQ ID NO 259
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 259
gcagcgtctc cttcccgttc                                                   20

<210> SEQ ID NO 260
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 260
ccagcttgtc cttcccgttc                                                   20

<210> SEQ ID NO 261
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 261
ccagcgtgtc cttcccgttc                                                   20

```
<210> SEQ ID NO 262
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 262
gcagcgtctc cttcccattc                                        20

<210> SEQ ID NO 263
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 263
gcagcgtctc cttcckgttc                                        20

<210> SEQ ID NO 264
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 264
tgtcatttct tcaatgggac                                        20

<210> SEQ ID NO 265
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 265
agtgtcattt cttcaacggg                                        20

<210> SEQ ID NO 266
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 266
gtgttatttc ttcaatggga                                        20

<210> SEQ ID NO 267
<211> LENGTH: 20
<212> TYPE: DNA
<213> ORGANISM: Artificial Sequence
```

```
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 267
gtgtcaattc ttcaatggga                                              20

<210> SEQ ID NO 268
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 268
gtgtcatttc ctcaatggga                                              20

<210> SEQ ID NO 269
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 269
ggagcgggtg cggttgctgg                                              20

<210> SEQ ID NO 270
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 270
ggagcgggtg cggtacctgg                                              20

<210> SEQ ID NO 271
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 271
ggagcgggtg cggttcctgg                                              20

<210> SEQ ID NO 272
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
```

```
<222> LOCATION: (1)..(20)

<400> SEQUENCE: 272
ggagcgggtg cgattcctgg                                              20

<210> SEQ ID NO 273
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 273
ggagcgggtg cggtatctgc                                              20

<210> SEQ ID NO 274
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 274
ggagcgggtg cggttactgg                                              20

<210> SEQ ID NO 275
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 275
acatctataa ccaagaggag                                              20

<210> SEQ ID NO 276
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 276
acatccataa acgggaggag                                              20

<210> SEQ ID NO 277
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 277
```
tataaccaag aggagtacgt                                           20

<210> SEQ ID NO 278
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 278
aaccccgtag ttgtgtctgc                                           20

<210> SEQ ID NO 279
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 279
aaccccgtag ttgtatctgc                                           20

<210> SEQ ID NO 280
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 280
cgtaattgta tctgcagtag                                           20

<210> SEQ ID NO 281
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 281
tagttgtcca cttcggcccg                                           20

<210> SEQ ID NO 282
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 282
cgctgcactg tgaagctctc                                           20

<210> SEQ ID NO 283

```
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 283
cgctgcaccg tgaagctctc                                               20

<210> SEQ ID NO 284
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 284
cctgtggaac tgagagagcc                                               20

<210> SEQ ID NO 285
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 285
caacgtcctc atctgtttca                                               20

<210> SEQ ID NO 286
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 286
ctgctgcatt gcttttgcgc                                               20

<210> SEQ ID NO 287
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 287
ttacagaggc cccctgcgtt                                               20

<210> SEQ ID NO 288
<211> LENGTH: 20
<212> TYPE: DNA
<213> ORGANISM: Artificial Sequence
<220> FEATURE:
```

```
<223> OTHER INFORMATION: Primer for PCR amplification
<220> FEATURE:
<221> NAME/KEY: primer_bind
<222> LOCATION: (1)..(20)

<400> SEQUENCE: 288
gtccagggca gggccactcc                                                20

<210> SEQ ID NO 289
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 289
aattacgtgt accagggacg                                                20

<210> SEQ ID NO 290
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 290
aattaccttt tccagggacg                                                20

<210> SEQ ID NO 291
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 291
aattacgtgt accagttacg                                                20

<210> SEQ ID NO 292
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 292
aattacgcgt accagttacg                                                20

<210> SEQ ID NO 293
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)
```

```
<400> SEQUENCE: 293
cggcctcgtc cagctcgtag                                           20

<210> SEQ ID NO 294
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 294
tgggcccgcc cagctcgtag                                           20

<210> SEQ ID NO 295
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 295
tgggcccgac cagctcgtag                                           20

<210> SEQ ID NO 296
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 296
ggactcggcg ctgcagggtc                                           20

<210> SEQ ID NO 297
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 297
aggagctggg gccatcaagg                                           20

<210> SEQ ID NO 298
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 298
gaccatgtgt caacttatgc                                           20
```

```
<210> SEQ ID NO 299
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 299
ctcaggggga tcgttggtgg                                                   20

<210> SEQ ID NO 300
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 300
ctcaggggga tcattggcgg                                                   20

<210> SEQ ID NO 301
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 301
cagctccaca ggctccttgg                                                   20

<210> SEQ ID NO 302
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 302
actctcccga ggatttcgtg                                                   20

<210> SEQ ID NO 303
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 303
tgtgctactt caccaacggg                                                   20

<210> SEQ ID NO 304
<211> LENGTH: 20
```

```
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 304
acctcgtagt tgtgtctgca                                          20

<210> SEQ ID NO 305
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 305
aactggtagt tgtgtctgca                                          20

<210> SEQ ID NO 306
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 306
actctcctct gcaggatccc                                          20

<210> SEQ ID NO 307
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 307
actcgccgct gcaaggtcgt                                          20

<210> SEQ ID NO 308
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 308
actctcctct gcaagatccc                                          20

<210> SEQ ID NO 309
<211> LENGTH: 20
<212> TYPE: DNA
<213> ORGANISM: Artificial Sequence
<220> FEATURE:
<223> OTHER INFORMATION: Primer for PCR amplification
```

```
<220> FEATURE:
<221> NAME/KEY: primer_bind
<222> LOCATION: (1)..(20)

<400> SEQUENCE: 309
tggtgtaaac ttgtaccagt                                               20

<210> SEQ ID NO 310
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 310
acccatgaat ttgatggaga                                               20

<210> SEQ ID NO 311
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 311
ggaacctcat tggtagcagc                                               20

<210> SEQ ID NO 312
<211> LENGTH: 20
<212> TYPE: DNA
<213> ORGANISM: Artificial Sequence
<220> FEATURE:
<223> OTHER INFORMATION: Primer for PCR amplification
<220> FEATURE:
<221> NAME/KEY: primer_bind
<222> LOCATION: (1)..(20)

<400> SEQUENCE: 312
acttggaaaa cactgtgacc                                               20
```